(12) United States Patent
Aifantis et al.

(10) Patent No.: US 9,101,559 B2
(45) Date of Patent: Aug. 11, 2015

(54) LEUKEMIC CELL CNS INFILTRATION CONTROLLED BY NOTCH-INDUCED CHEMOTAXIS

(75) Inventors: Iannis Aifantis, Brooklyn, NY (US); Silvia Buonamici, Boston, MA (US)

(73) Assignee: New York University, New York, NY (US)

(*) Notice: Subject to any disclaimer, the term of this patent is extended or adjusted under 35 U.S.C. 154(b) by 425 days.

(21) Appl. No.: 12/776,920

(22) Filed: May 10, 2010

(65) Prior Publication Data

US 2010/0285020 A1    Nov. 11, 2010

Related U.S. Application Data

(60) Provisional application No. 61/176,713, filed on May 8, 2009.

(51) Int. Cl.

| | |
|---|---|
| A61K 38/02 | (2006.01) |
| A61K 31/00 | (2006.01) |
| A61K 31/439 | (2006.01) |
| A61K 31/519 | (2006.01) |
| A61K 31/704 | (2006.01) |
| G01N 33/50 | (2006.01) |
| A61K 31/573 | (2006.01) |
| A61K 31/7068 | (2006.01) |
| A61K 31/7088 | (2006.01) |
| A61K 38/50 | (2006.01) |
| A61K 45/06 | (2006.01) |
| G01N 33/574 | (2006.01) |

(52) U.S. Cl.
CPC .................. *A61K 38/02* (2013.01); *A61K 31/00* (2013.01); *A61K 31/439* (2013.01); *A61K 31/519* (2013.01); *A61K 31/573* (2013.01); *A61K 31/704* (2013.01); *A61K 31/7068* (2013.01); *A61K 31/7088* (2013.01); *A61K 38/50* (2013.01); *A61K 45/06* (2013.01); *G01N 33/5041* (2013.01); *G01N 33/57426* (2013.01); *G01N 2500/10* (2013.01)

(58) Field of Classification Search
None
See application file for complete search history.

(56) References Cited

U.S. PATENT DOCUMENTS

2002/0168358 A1* 11/2002 Gladue et al. ............. 424/131.1
2009/0312396 A1* 12/2009 Byth et al. ................. 514/44 A

FOREIGN PATENT DOCUMENTS

| WO | 2004/104574 A2 | 12/2004 | |
|---|---|---|---|
| WO | 2007/003216 | 11/2007 | |
| WO | WO2008112249 | * 9/2008 | ........... C07D 345/00 |

OTHER PUBLICATIONS

De Keersmaecker et al. In vitro validation of gamma-secretase inhibitors alone or in combination with other anti-cancer drugs for the treatment of T-cell acute lymphoblastic leukemia. Haematologica. Apr. 2008;93(4):533-42. Epub Mar. 5, 2008.*
Larson et al. A five-drug remission induction regimen with intensive consolidation for adults with acute lymphoblastic leukemia: cancer and leukemia group B study 8811. Blood. Apr. 15, 1995;85(8):2025-37.*
Mauro et al. Autoimmune hemolytic anemia in chronic lymphocytic leukemia: clinical, therapeutic, and prognostic features. Blood. May 1, 2000;95(9):2786-92.*
Till et al. The chemokine receptor CCR7 and alpha4 integrin are important for migration of chronic lymphocytic leukemia cells into lymph nodes. Blood. Apr. 15, 2002;99(8):2977-84.*
Akers et al. VE-cadherin and PECAM-1 enhance ALL migration across brain microvascular endothelial cell monolayers. Exp Hematol. Sep. 2010;38(9):733-43. Epub May 12, 2010.*
Pan et al. 2008 "Tubocapsanolide a Inhibits Transforming Growth Factor-β-activating Kinase 1 to Suppress NF-kB-induced CCR7" J Biol Chem 284:2746-2754.*
Kress et al., "Cell Surface Markers in HTLV-1 Pathogenesis," Viruses 3:1439-1459 (2011).
Graux, "Biology of Acute Lymphoblastic Leukemia (ALL): Clinical and Therapeutic Relevance," Transfus. Apher. Sci. 44:183-189 (2011).
Aifantis et al., "Molecular Pathogenesis of T-Cell Leukaemia and Lymphoma," Nature Rev. Immunol. 8(5):380-390 (2008).
Shields et al., "Autologous Chemotaxis as a Mechanism of Tumor Cell Homing to Lymphatics via Interstitial Flow and Autocrine CCR7 Signaling," Cancer Cell 11:526-538 (2007).
Muller et al., "Involvement of Chemokine Receptors in Breast Cancer Metastasis," Nature 410:50-56 (2001).
Buonamici et al., "CCR7 Signalling as an Essential Regulator of CNS Infiltration in T-Cell Leukaemia," Nature 459:1000-1005, Supplementary Information (13 pages) (2009).

* cited by examiner

*Primary Examiner* — Gregory S Emch
*Assistant Examiner* — Adam M Weidner
(74) *Attorney, Agent, or Firm* — LeClairRyan, a Professional Corporation

(57) ABSTRACT

The present invention is directed to methods of preventing central nervous system leukemia, treating T-cell acute lymphoblastic leukemia, and treating immune system disorders associated with CCR7-CCL19 mediated signaling. Suitable therapeutic agents for inhibiting CCR7-CCL19 signaling and methods of identifying additional therapeutic agents useful in the methods of the present invention are also disclosed.

8 Claims, 30 Drawing Sheets

| | | | |
|---|---|---|---|
| -2.7 | Adam15 | 1.7 | Icam2 |
| 2.4 | Adam8 | 1.9 | Ilk |
| 10.2 | Cak | 1.7 | Itga2b |
| 4.3 | Ccl22 | 2.0 | Itga3 |
| 3.5 | Ccl24 | -2.7 | Itga6 |
| 3.8 | Ccl3 | 4.4 | Itgae |
| 8.6 | Ccl4 | -4.5 | Itgam |
| 28.0 | Ccl5 | 25.7 | Itgax |
| -10.8 | Ccl6 | 1.6 | Itgb1 |
| -5.4 | Ccl9 | -17.0 | Itgb21 |
| 1.7 | Ccr1 | 1.4 | Itgb5 |
| -7.8 | Ccr2 | 3.8 | Itgb7 |
| 1.8 | Ccr6 | -2.0 | Itgp |
| 27.8 | Ccr7 | 14.5 | Mmp13 |
| 9.1 | Cdh1 | 16.1 | Mmp14 |
| -1.6 | Cklf | -14.3 | Mmp8 |
| 10.8 | Cx3cl1 | 1.9 | Mmp9 |
| 26.7 | Dtx1 | 10.4 | Nrarp |
| 8.0 | Gata3 | 1.6 | Sdf4 |
| 46.1 | Hey1 | 1.6 | Selpl |

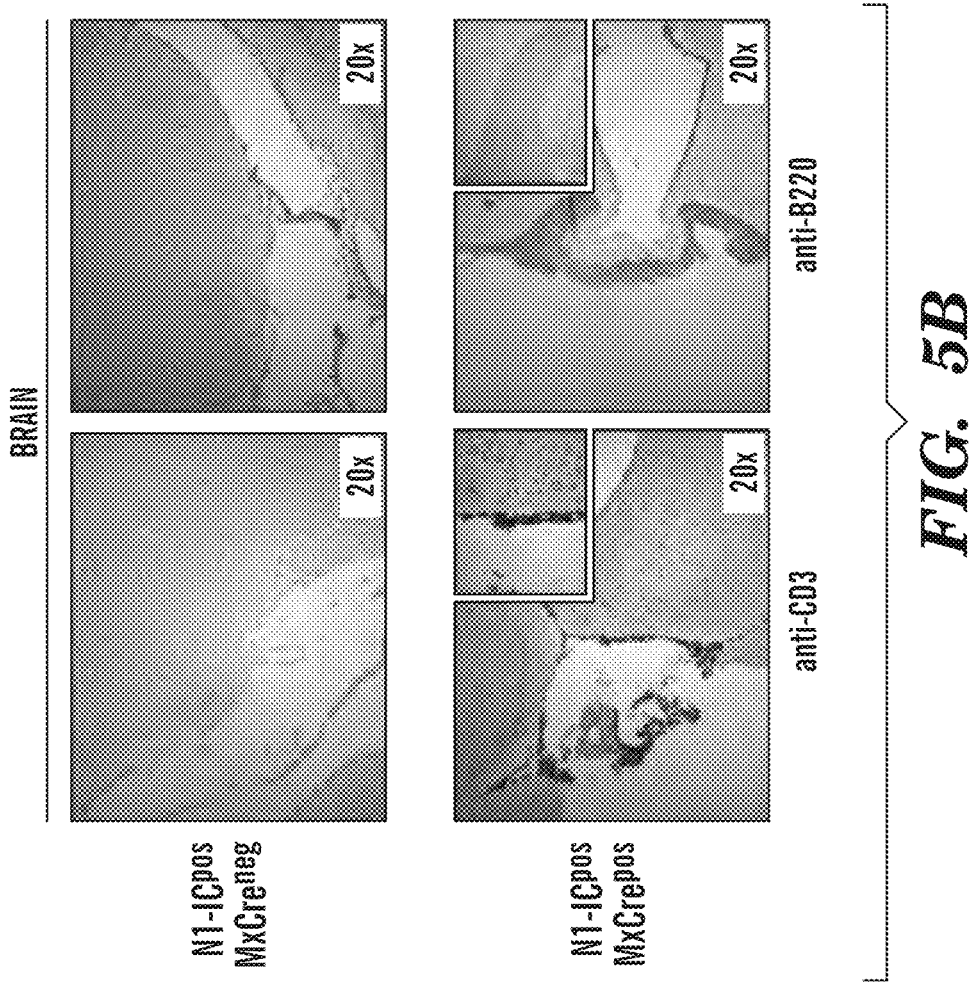

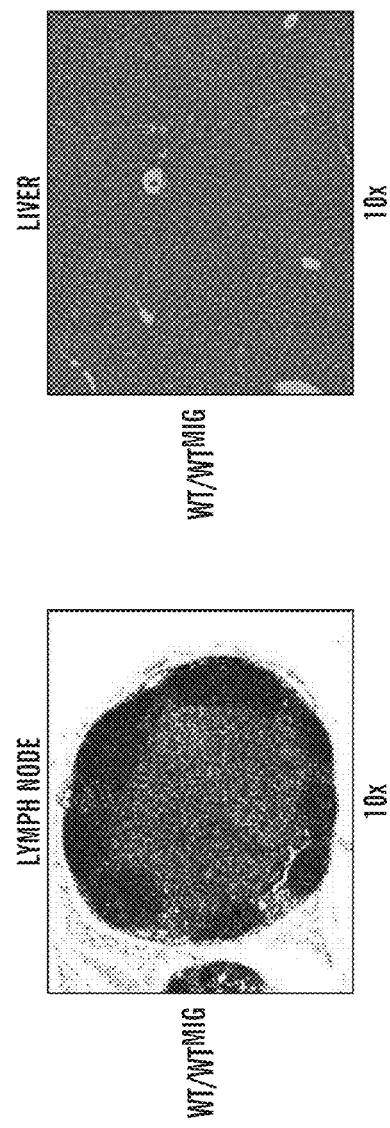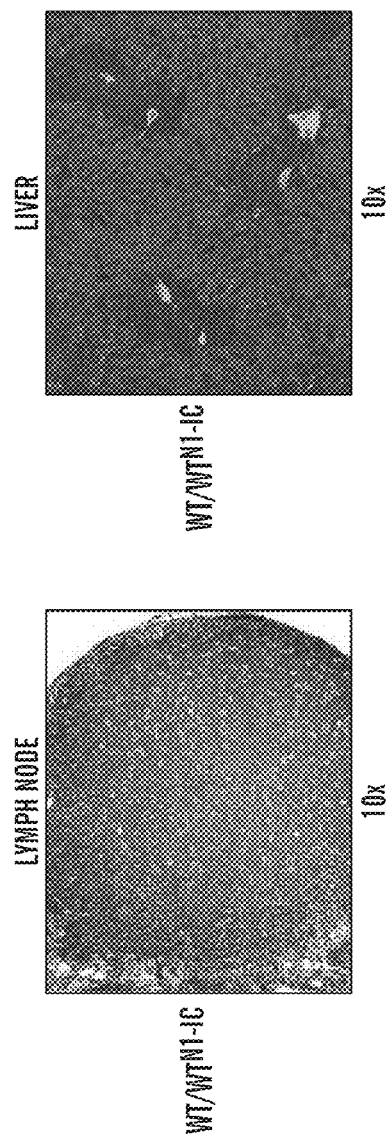
FIG. 6B  
FIG. 6D  
FIG. 6A  
FIG. 6C

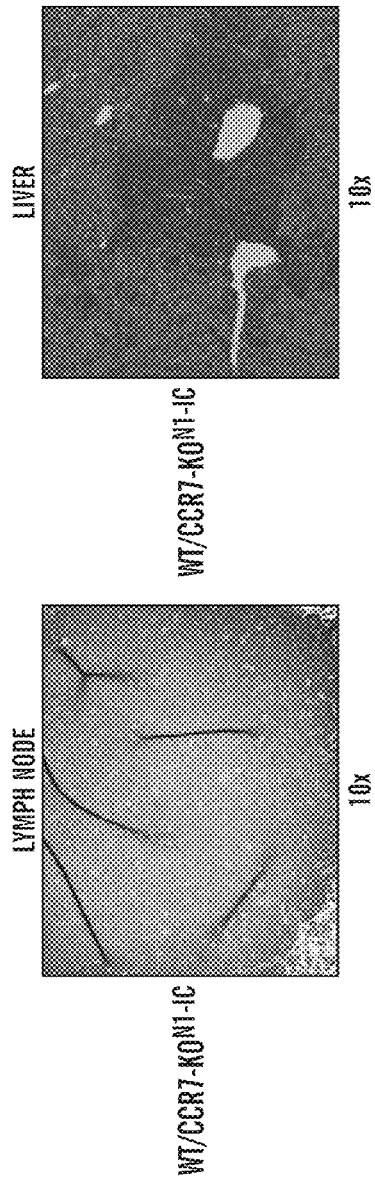
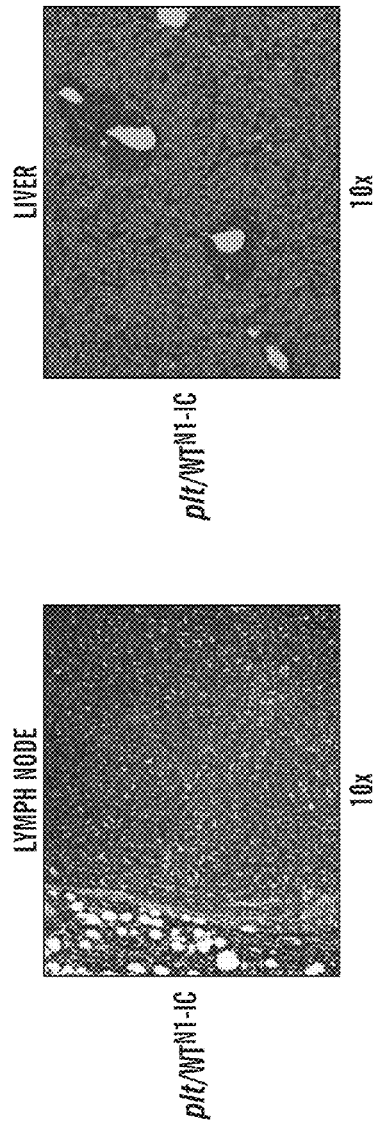

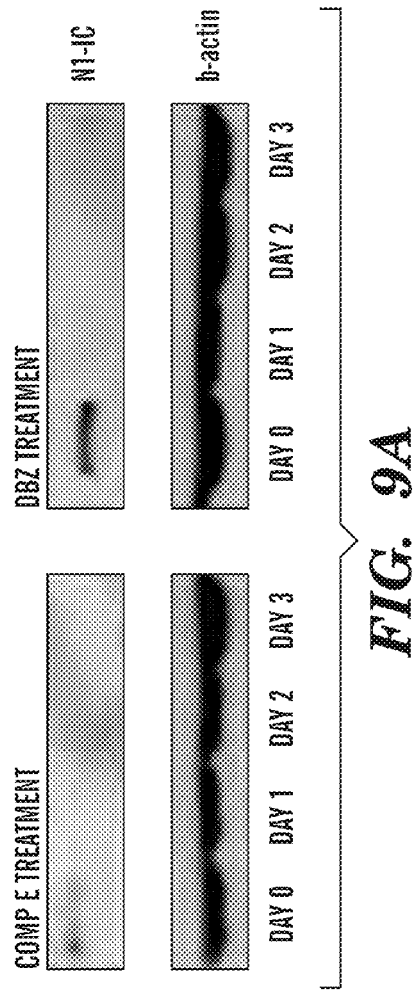
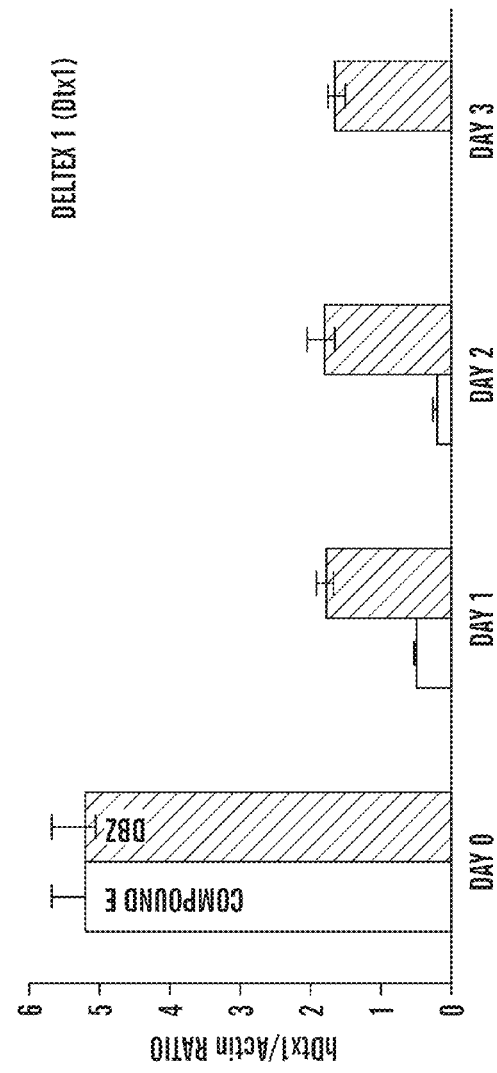
FIG. 9A
FIG. 9B

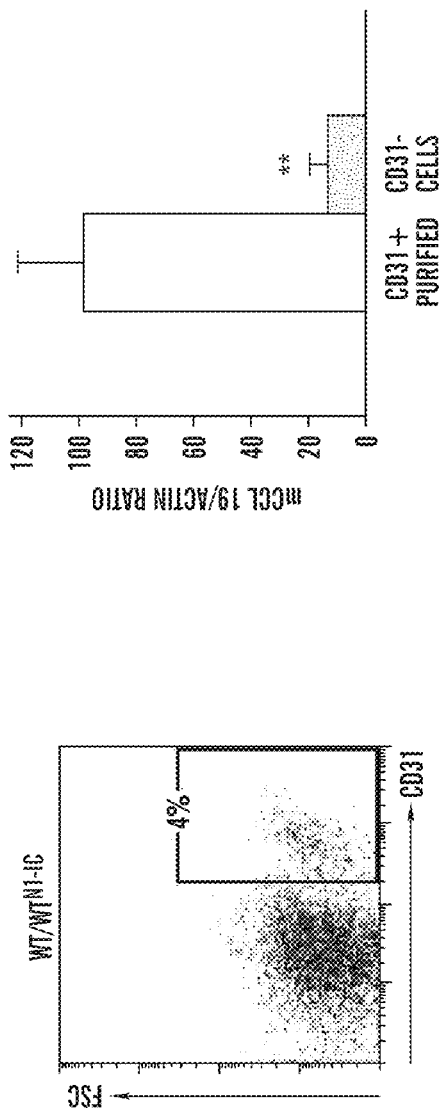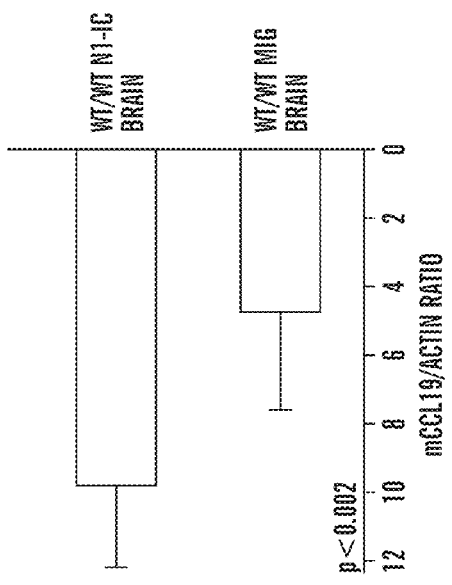
FIG. 15A
FIG. 15B
FIG. 16A

LEUKEMIC CELL CNS INFILTRATION CONTROLLED BY NOTCH-INDUCED CHEMOTAXIS

This application claims the benefit of U.S. Provisional Patent Applicfixed. esation Ser. No. 61/176,713, filed May 8, 2009, which is hereby incorporated by reference in its entirety.

This invention was made with government support under grant numbers RO1CA105129, RO1CA133379, P30CA016087, 1RO1CA149655, and 1R21CA141399 awarded by the National Institutes of Health. The government has certain rights in this invention.

FIELD OF THE INVENTION

The present invention is directed to methods of preventing central nervous system leukemia and treating immune system disorders associated with CCR7-CCL19 mediated signaling.

BACKGROUND OF THE INVENTION

T-cell acute lymphoblastic leukemia (T-ALL) is a blood malignancy afflicting mainly children and adolescents (Grabber et al., "Notch-1 Activation in the Molecular Pathogenesis of T-Cell Acute Lymphoblastic Leukaemia," *Nat Rev Cancer* 6(5):347-59 (2006)). T-ALL patients present at diagnosis with elevated white cell counts, hepatosplenomegaly, and are at elevated risk for central nervous system (CNS) relapse (Aifantis et al., "Molecular Pathogenesis of T-cell Leukemia and Lymphoma," *Nat Rev Immunol* 8:380-90 (2008) and Pui et al., "Current Management and Challenges of Malignant Disease in the CNS in Pediatric Leukemia," *Lancet Oncol* 9:257-68 (2008)). For this reason, T-ALL patients usually receive cranial irradiation in addition to intensified intrathecal chemotherapy. The dramatic increase in survival is thought to be worth the significant side effects associated with this therapy. Such complications include secondary tumors, neurocognitive deficits, endocrine disorders and growth impairment (Pui et al., "Current Management and Challenges of Malignant Disease in the CNS in Pediatric Leukemia," *Lancet Oncol* 9:257-68 (2008)). Unfortunately, little is known about the mechanism of leukemic cell infiltration on the CNS or how it can be prevented despite its clinical significance.

The present invention is directed to overcoming these and other deficiencies in the art.

SUMMARY OF THE INVENTION

A first aspect of the present invention is directed to a method of preventing central nervous system leukemia in a subject. This method involves selecting a subject at risk for developing central nervous system leukemia and providing a therapeutic agent that inhibits CCR7-CCL19 signaling. The method further involves administering the therapeutic agent to the selected subject under conditions effective to prevent central nervous system leukemia in the selected subject.

A second aspect of the present invention is directed to a method of treating T-cell acute lymphoblastic leukemia in a subject. This method involves selecting a subject having T-cell acute lymphoblastic leukemia and administering a cocktail of chemotherapeutic agents and a therapeutic agent that inhibits CCR7-CCL19 signaling under conditions effective to treat T-cell acute lymphoblastic leukemia in the selected subject.

Another aspect of the present invention relates to a method of treating an immune system disorder in a subject. This method involves selecting a subject having an immune system disorder and providing a therapeutic agent that inhibits CCR7-CCL19 signaling. The method further involves administering the therapeutic agent to the selected subject under conditions effective to treat the immune system disorder in the selected subject.

Another aspect of the present invention is directed to a method of identifying a compound capable of preventing leukocyte transendothelial cell migration. This method involves providing one or more candidate compounds and contacting the one or more candidate compounds with a CCR7-CCL 19 signaling system. The method further involves determining whether the one or more candidate compounds inhibits CCR7-CCL19 mediated signaling, and identifying the one or more candidate compounds which inhibit CCR7-CCL19 mediated signaling as a compound capable of preventing leukocyte transendothelial cell migration.

The present invention has potential importance in the treatment of patients at risk of developing or having developed central nervous system (CNS) leukemia. Current treatments of leukemia patients with CNS infiltration include cranial irradiation and intrathecal chemotherapy. Both these treatments have significant side effects (including secondary tumors, growth retardation, etc). Targeting the CCR7-CCL 19 interaction is a novel therapeutic approach having potentially minimal side-effects.

BRIEF DESCRIPTION OF THE DRAWINGS

FIG. 2A is a heat diagram of selected adhesion/migration regulators that are controlled by Notch-1 (N1-IC) expression in hematopoietic progenitor cells. A few classical Notch targets (Dtx1, Gata3, Hey1, Nrarp) are included. For all genes, p<0.001. Color-coding is as follows: Yellow indicates increased mRNA abundance, blue indicates decreased mRNA abundance. Real time PCR (FIG. 2B) and FACS analysis (FIG. 2C) show the induction of CCR7 gene and protein expression, respectively, in hematopoietic progenitor cells in response to N1-IC expression (n=4). FIG. 2D is a graph illustrating N1-IC expression induced chemotaxis of wild-type (WT$^{N1-IC}$), but not CCR7-knockout progenitor cells expressing Notch-1 (CCR7-KO$^{N1-IC}$) towards both CCL19 and CCL21 (n=3). WT$^{MIG}$ and CCR7-KO$^{MIG}$ represent control cells. Error bars define standard deviation from mean for all experiments (FIGS. 2B-2D).

FIG. 3A is a Kaplan-Meyer analysis of recipient animals that received identical numbers of the human T-ALL cells expressing CCR7 (CEM/CCR7$^{pos}$ and DND41/mCCR7$^{pos}$) or lacking CCR7 expression (DND41/CCR7$^{neg}$), n=5. FIG. 3B is a panel of bioluminescent images of mice 2 weeks post-transplantation with DND41/CCR7$^{neg}$, CEM/CCR7$^{pos}$, DND41/mCCR7$^{pos}$, or control cell lines. Infiltration of T-ALL cells into the CNS of CEM/CCR7$^{pos}$ and DND41/mCCR7$^{pos}$, but not DND41/CCR7$^{neg}$ recipient mice was observed by bioluminescence imaging (FIG. 3C) and histochemical analysis (FIG. 3D).

FIG. 4A are immunohistochemical images showing leukemic cells in the brain meningeal spaces of the indicated transplanted recipients. Plt mice, deficient in CCL19 expression, were transplanted with wildtype hematopoietic cells containing the Notch-1 construct (plt/WT$^{N1-IC}$) and wildtype mice were transplanted with hematopoietic cells deficient in CCR7 expression (CCR7-KO) containing the Notch-I construct (WT/CCR7-KO$^{N1-IC}$). Leukemic cell infiltration of the brain meningeal space in positive (WT/WT$^{N1-IC}$) and negative (WT/WT$^{MIG}$) control recipient mice is also shown. FIGS. 4B-4G are immunofluorescence images of brain sections showing magnification of a brain microvessel in plt/WT$^{N1-IC}$ (FIGS. 4B and 4D) and WT/WT$^{N1-IC}$ (FIGS. 4C and 4E) mice. Endothelial CD31$^+$ cells are shown in blue. CCL19 expression (shown in red) was observed in WT/WT$^{N1-IC}$ (FIG. 4E) but not plt/WT$^{N1-IC}$ (FIG. 4D) microvessels. Magnification of a WT/WT$^{N1-IC}$ microvessel is shown in FIG. 4F and co-staining of CCL19 (red) and CD31 (blue) in this microvessel is shown in FIG. 4G.

FIGS. 5A-5B show the induction of T-ALL in the cre-inducible EF1a-N1-IC animal model. In FIG. 5A, peripheral blood CD4/CD8 FACS staining (left panel), lymph node hematoxylin and eosin (H&E) (middle panel), and CD3 staining (right panel) is shown. FIG. 5B is a panel of immunohistochemical images showing CD3$^+$ (left) B220$^-$ (right) cell staining in the brain meningeal spaces of Mx-cre$^{pos}$/N1-IC$^{neg}$ (top) and Mx-cre$^{pos}$/N1-IC$^{pos}$ (bottom) mice. In all cases, a representative of more than 5 individual experiments is shown.

FIGS. 6A-6H are histopathological images showing the infiltration of N1-IC+ leukemic cells into lymph node (FIGS. 6A, 6C, 6E, and 6G) and liver tissue (FIGS. 6B, 6D, 6F, and 6H) of WT/WT$^{MIG}$ (FIGS. 6A-6B), WT/WT$^{N1-IC}$ (FIGS. 6C-6D), WT/CCR7-KO$^{N1-IC}$ (FIGS. 6E-6F), and plt/WT$^{N1-IC}$ (FIGS. 6G-6H) recipient mice.

FIG. 7C shows the appearance of infiltrating N1-IC/EGFP+ lymphocytes at 19 days post transplant (n=3 for each genotype).

FIGS. 9A-9D show γ-secretase-inhibitor mediated suppression of CCR7 expression. CEM cells (T-ALL cell line) were treated with either Compound E (Comp E) (1 nM) or DBZ (1 nM) for three days. FIG. 9A is a panel of western blots showing the disappearance of the activated N1-IC protein in CEM cells following γ-secretase inhibitor (GSI) treatment. β-actin immunoreactivity is shown as a loading control. GSI treatment efficiently suppressed the transcription of both Dtx1 (FIG. 9B) and Hes1 (FIG. 9C), two well-characterized Notch target genes in T-cells. GSI treatment also suppressed transcription of human CCR7 (FIG. 9D). Error bars define standard deviation from mean.

FIG. 13B is a panel of histopathological images showing the detection of infiltrating B220+ lymphocytes in the meningeal spaces of wildtype (WT) recipients transplanted with either MLL-ENL or BCR-ABL expressing cells co-expressing the CCR7 receptor (WT/WT BCR-ABL and WT/WT MLL-ENL; upper and lower left images of FIG. 13B, respectively) or lacking CCR7 receptor expression (WT/CCR7-KO BCR-ABL and WT/CCR7-KO MLL-ENL; upper and lower right images of FIG. 13B, respectively).

FIGS. 15A-15B show CCL19 mRNA expression in brain endothelial cells. Purification of CD31+ cells from leukemic mouse brain is shown in FIG. 15A. CD31+ endothelial cells express elevated levels of CCL19 mRNA when compared to CD31− cells from the identical leukemic brain (FIG. 15B). One of three representative experiments is shown. Error bars define standard deviation from mean.

FIGS. 16A-16C demonstrate the failure of CD4+ T-cells to infiltrate the CNS in short-term (16h) transplantation assays. A higher level of CCL19 mRNA expression in CD31+ endothelial cells purified from leukemic brains (p<0.002) compared to non-leukemic brains was observed (FIG. 16A). This is a representative of three individual experiments. The successful engrafting of CD4+ CMRA+ (orange dye) cells in peripheral blood and lymph nodes of transplanted, non irradiated syngeneic recipients, 16 h post transplantation is shown in the scatterplots of FIG. 16B. FIG. 16C shows the presence of infiltrating leukemic N1-IC/EGFP+ but not WT CD4+ CMRA+ T-cells 16 h post transplantation (n=4, for both leukemic and wild type non-irradiated hosts). At least 500 N1-IC/EGFP+ cells were counted and no CD4+ CMRA+ cells were found. WT CD4+ CMRA+ were readily detected using microscopy in different tissues including the lymph nodes and the spleen.

DETAILED DESCRIPTION OF THE INVENTION

Figure 1A:
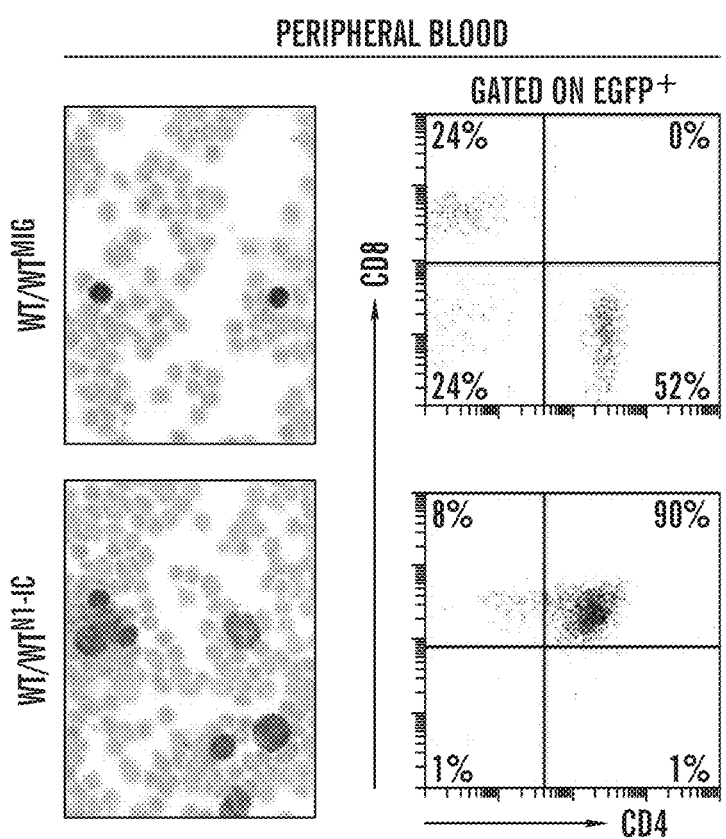
FIGS. 1A-1C demonstrate that Notch 1 activation induces T-ALL and targets leukemic cells into the CNS. The peripheral blood smears and FACS staining using CD4/CD8 antibodies shown in FIG. 1A indicate the induction of T-ALL in a mouse transplantation model. In this model, wildtype (WT) hematopoietic progenitor cells carrying oncogenic Notch 1 (N1-IC) (with EGFP-tag) were introduced into a recipient wildtype mouse by retroviral transfer (WT/WT$^{N1-IC}$). WT/WT$^{MIG}$ are control mice. N1-IC$^+$EGFP$^+$ cells in the brain meningeal spaces of transplanted mice are shown in FIG. 1B (lower panel), but not in control mice (FIG. 1B; upper panel). Infiltrating lymphocytes were observed surrounding a brain vessel in leukemic (FIG. 1C; lower panel) but not healthy (control) recipients (FIG. 1C; top panel). Co-staining with CD31 antibodies (blue) indicates endothelial cells within the infiltrating lymphocytes.

A first aspect of the present invention is directed to a method of preventing central nervous system (CNS) leukemia in a subject. This method involves selecting a subject at risk for developing CNS leukemia and providing a therapeutic agent that inhibits CCR7-CCL19 signaling. The method further involves administering the therapeutic agent to the selected subject under conditions effective to prevent CNS leukemia in the selected subject.

In accordance with this aspect of the present invention, a subject at risk for developing CNS leukemia is a subject having any form of acute or chronic leukemia. "Leukemia" as used herein refers to any cancer of the blood or bone marrow that is characterized by an abnormal proliferation of blood cells, usually white blood cells. Accordingly, a subject at risk for developing CNS leukemia includes a subject having acute lymphoblastic leukemia, chronic lymphocytic leukemia, acute myelogenous leukemia, acute lymphoblastic leukemia, hairy cell leukemia, and T-cell prolymphocytic leukemia. In a preferred embodiment, the subject at risk for developing central nervous system leukemia has T-cell acute lymphoblastic leukemia.

As used herein, "subject" refers to any animal at risk for developing CNS leukemia or any other condition described infra, which is amenable to treatment in accordance with the methods of the present invention. Preferably, the subject is a mammal. Exemplary mammalian subjects include, without limitation, humans, non-human primates, dogs, cats, rodents (e.g., mouse, rat, guinea pig), horses, cattle and cows, sheep, and pigs.

Therapeutic agents of the present invention are agents that inhibit the chemokine receptor-chemokine interaction of CCR7-CCL19 and/or the subsequent molecular signaling pathway triggered by the CCR7-CCL19 interaction.

Chemokines, including CCL19, function at least in part, by modulating a complex and overlapping set of biological activities important for the movement of lymphoid cells, and extravasation and tissue infiltration of leukocytes in response to inciting agents. These chemotactic cytokines, or chemokines, constitute a family of proteins, approximately 8-10 kDa in size, that are expressed by a wide variety of cells, to attract macrophages, T-cells, eosinophils, basophils, and neutrophils to sites of inflammation, and play a role in the maturation of cells of the immune system. CCL19 is known to play an important role in trafficking T-cells in the thymus, and in T-cell and B-cell migration to secondary lymphoid organs. CCL19 is the ligand to chemokine receptor CCR7. The nucleotide and amino acid sequences of the human CCL19 are well known in the art (NCBI Reference Sequences NM_006274 and NP_006265, respectively) and are hereby incorporated by reference in their entirety.

Chemokine receptors are cell-surface receptors belonging to the family of G-protein-coupled seven-transmembrane proteins that mediate the biological activity of chemokines. Chemokine receptors are classified based upon the chemokine that constitutes the receptor's natural ligand. A multitude of chemokine receptors have been characterized and are well known in the art. CCR7, the chemokine receptor for CCL19, is expressed on T-cells, B-cells, and mature dendritic cells. The nucleotide and amino acid sequences of the human CCR7 are well known in the art (NCBI Reference Sequences NM_001838 and NP_001829, respectively) and are hereby incorporated by reference in their entirety.

A therapeutic agent of the present invention includes any agent that inhibits CCR7-CCL19 signaling. Suitable agents include agents that inhibit CCR7-CC19 signaling directly by inhibiting the CCR7-CCL19 binding interaction. Alternatively, suitable therapeutic agents include agents that inhibit CCR7-CCL19 signaling indirectly by inhibiting the downstream molecular signaling pathway that is triggered subsequent to the CCR7-CCL19 interaction. In one embodiment of the present invention, the therapeutic agent is an inhibitor of CCL19. In another embodiment of the present invention, the therapeutic agent is an antagonist of CCR7. Suitable CCL19 inhibitors and CCR7 antagonists include nucleic acid inhibitory molecules, inhibitory peptides, antibodies, and small molecules, each of which is described in more detail below.

Exemplary nucleic acid CCL19 inhibitors and CCR7 antagonists include antisense RNAs or RNAi, such as short interfering RNAs (siRNA), short hairpin RNAs (shRNA), and microRNAs.

The use of antisense methods to inhibit the in vivo translation of genes and subsequent protein expression is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, H. M., "Antisense DNA and RNA," *Scientific Am.* 262:40-46 (1990), which is hereby incorporated by reference in its entirety). The antisense nucleic acid molecule hybridizes to its corresponding target nucleic acid molecule, such as the CCL19 or CCR7 mRNA, to form a double-stranded molecule, which interferes with translation of the mRNA, as the cell will not translate a double-stranded mRNA. Antisense nucleic acids used in the methods of the present invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the CCL19 or CCR7 nucleotide sequence (NCBI sequence reference numbers for the nucleotide sequences of CCL19 and CCR7 are provided supra). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. siRNA molecules that effectively interfere with CCL19 or CCR7 expression have been developed (e.g., Santa Cruz Biotechnology, Inc.) and are suitable for use in the present invention. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. shRNA molecules that effectively interfere with CCL19 or CCR7 expression have been developed (OriGene, Rockville, Md.) and are suitable for use in the methods of the present invention.

Nucleic acid aptamers that specifically bind to CCL19 or CCR7 are also useful in the methods of the present invention. Nucleic acid aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

Therapeutic agents that inhibit CCR7-CCL19 signaling of the present invention also include inhibitory peptides. Suitable inhibitory peptides of the present invention include modified CCL19 peptides that bind, preferably, specifically to the CCR7 protein but prevent normal CCR7-CCL19 signaling. In a preferred embodiment, the modified CCL19 peptide has an N-terminal truncation or extension that abrogates its signaling activity while preserving its binding properties. Such inhibitory peptides may be chemically synthesized using known peptide synthesis methodology or may be prepared and purified using recombinant technology. Such peptides are usually at least about 5 amino acids in length, but can be anywhere from 5 to 100 amino acids in length. Such peptides may be identified without undue experimentation using well known techniques. Techniques for screening peptide libraries for peptides that are capable of specifically binding to a polypeptide target, in this case CCR7, are well known in the art (see e.g., U.S. Pat. No. 5,556,762 to Pinilla et al.; U.S. Pat. No. 5,750,373 to Garrard et al.; U.S. Pat. No. 4,708,871 to Geysen; U.S. Pat. No. 4,833,092 to Geysen; U.S. Pat. No. 5,223,409 to Ladner et al.; U.S. Pat. No. 5,403,484 to Ladner et al.; U.S. Pat. No. 5,571,689 to Heuckeroth et al.; U.S. Pat. No. 5,663,143 to Ley et al.; and PCT Publication Nos. WO84/03506 to Geysen and WO84/03564 to Geysen, which are hereby incorporated by reference in their entirety).

In a preferred embodiment of the present invention, the therapeutic agent that inhibits CCR7-CCL19 signaling is an antibody. An antibody of the present invention encompasses any immunoglobulin molecule that specifically binds to an epitope of CCL19 or CCR7. As used herein, "epitope" refers to a region of the CCL19 or CCR7 protein that is recognized by the isolated antibody and involved in mediating the binding interaction between CCL19 and CCR7, or involved in mediating the downstream molecular signaling pathway triggered by the CCR7-CCL19 binding interaction. In a preferred embodiment, the antibody of the present invention has antigen specificity to the extracellular domain of CCL19. In another embodiment, the antibody of the present invention has antigen specificity to the extracellular domain of the CCR7. Suitable CCR7 antibodies and methods of making the same are disclosed in WO2004/104574 to Golz et al., and WO2007/003216 to Calleja et al., which are hereby incorporated by reference in their entirety.

The epitope recognized by the antibody of the present invention may be a linear epitope, i.e. the primary structure of the amino acid sequence of CCR7 or CCL19. Alternatively, the epitope recognized by the isolated antibody of the present invention is a non-linear or conformational epitope, i.e. the tertiary or quaternary structure of the CCL19 or CCR7 proteins.

As used herein, the term "antibody" is meant to include intact immunoglobulins derived from natural sources or from recombinant sources, as well as immunoreactive portions (i.e. antigen binding portions) of intact immunoglobulins. The antibodies of the present invention may exist in a variety of forms including, for example, polyclonal antibodies, monoclonal antibodies, intracellular antibodies, antibody fragments (e.g. Fv, Fab and F(ab)2), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," Proc Natl Acad Sci USA 85:5879-5883 (1988); Bird et al, "Single-Chain Antigen-Binding Proteins," Science 242: 423-426 (1988), which are hereby incorporated by reference in their entirety).

Methods for monoclonal antibody production may be carried out using techniques well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., an epitope of CCL19 or CCR7) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," Eur J Immunol 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Alternatively monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, generate monoclonal antibodies. Alternatively, recombinant monoclonal antibodies or fragments thereof of the desired species can be isolated from phage display libraries (McCafferty et al., "Phage Antibodies: Filamentous Phage Displaying Antibody Variable Domains," Nature 348:552-554 (1990); Clackson et al., "Making Antibody Fragments using Phage Display Libraries," Nature 352:624-628 (1991); and Marks et al., "By-Passing Immunization. Human Antibodies from V-Gene Libraries Displayed on Phage," J. Mol. Biol. 222:581-597 (1991), which are hereby incorporated by reference in their entirety).

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimum to no non-human sequences.

An antibody can be humanized by substituting the complementarity determining region (CDR) of a human antibody with that of a non-human antibody (e.g., mouse, rat, rabbit, hamster, etc.) having the desired specificity, affinity, and capability (Jones et al., "Replacing the Complementarity-Determining Regions in a Human Antibody With Those From a Mouse," Nature 321:522-525 (1986); Riechmann et al., "Reshaping Human Antibodies for Therapy," Nature 332: 323-327 (1988); Verhoeyen et al., "Reshaping Human Antibodies: Grafting an Antilysozyme Activity," Science 239: 1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Human antibodies can be produced using various techniques known in the art. For example, immortalized human B lymphocytes immunized in vitro or isolated from an immunized individual that produce an antibody directed against a target antigen can be generated (see e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, human antibodies can be selected from a phage library that expresses human antibodies (Vaughan et al., "Human Antibodies with Sub-Nanomolar Affinities Isolated from a Large Non-immunized Phage Display Library," Nature Biotechnology, 14:309-314 (1996); Sheets et al., "Efficient Construction of a Large Nonimmune Phage Antibody Library: The Production of High-Affinity Human Single-Chain Antibodies to Protein Antigens," Proc. Natl. Acad. Sci. U.S.A. 95:6157-6162 (1998); Hoogenboom et al., "By-passing Immunisation. Human Antibodies From Synthetic Repertoires of Germline VH Gene Segments Rearranged In Vitro," J Mol Biol 227: 381-8 (1992); Marks et al., "By-passing Immunization. Human Antibodies from V-gene Libraries Displayed on Phage," J Mol Biol 222:581-97 (1991), which are hereby incorporated by reference in their entirety). Human antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety Procedures for raising polyclonal antibodies are also well known.

Typically, such antibodies can be raised by administering the peptide or polypeptide containing the epitope of interest subcutaneously to New Zealand white rabbits which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

In addition to whole antibodies, the present invention encompasses binding portions of such antibodies. Such binding portions include the monovalent Fab fragments, Fv fragments (e.g., single-chain antibody, scFv), single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES:PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

The present invention also encompasses the use of bispecific humanized antibodies or bispecific antigen-binding fragments (e.g., F(ab')$_2$) which have specificity for CCL19 or CCR7 and a molecule expressed on a target cell (e.g., leukemic T-cells or CNS endothelial cells). Techniques for making bispecific antibodies are common in the art (Brennan et al., "Preparation of Bispecific Antibodies by Chemical Recombination of Monoclonal Immunoglobulin G1 Fragments," *Science* 229:81-3 (1985); Suresh et al, "Bispecific Monoclonal Antibodies From Hybrid Hybridomas," *Methods in Enzymol.* 121:210-28 (1986); Traunecker et al., "Bispecific Single Chain Molecules (Janusins) Target Cytotoxic Lymphocytes on HIV Infected Cells," *EMBO J.* 10:3655-3659 (1991); Shalaby et al., "Development of Humanized Bispecific Antibodies Reactive with Cytotoxic Lymphocytes and Tumor Cells Overexpressing the HER2 Protooncogene," *J. Exp. Med.* 175:217-225 (1992); Kostelny et al, "Formation of a Bispecific Antibody by the Use of Leucine Zippers," *J. Immunol.* 148: 1547-1553 (1992); Gruber et al., "Efficient Tumor Cell Lysis Mediated by a Bispecific Single Chain Antibody Expressed in *Escherichia coli,*" *J. Immunol.* 152: 5368-74 (1994); and U.S. Pat. No. 5,731,168 to Carter et al., which are hereby incorporated by reference in their entirety). Generally, bispecific antibodies are secreted by triomas (i.e., lymphoma cells fuse to a hybridoma) and hybrid hybridomas. The supernatants of triomas and hybrid hybridomas can be assayed for bispecific antibody production using a suitable assay (e.g., ELISA), and bispecific antibodies can be purified using conventional methods. These antibodies can then be humanized according to methods known in the art. Humanized bispecific antibodies or a bivalent antigen-binding fragment of the bispecific antibody having binding specificity for CCL19 or CCR7 and an antigen expressed on a target cell, provides a cell-specific targeting approach.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention also encompasses the nucleic acid molecules that encode the CCL19 or CCR7 antibodies of the invention. The nucleic acids may be present in whole cells, in a cell lysate, or in a partially purified or substantially pure form (i.e., purified away from other cellular components or other contaminants).

Nucleic acids encoding the antibodies of the present invention can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g., using phage display techniques), the nucleic acid encoding the antibody can be recovered from the library.

Preferred nucleic acid molecules of the invention are those encoding the $V_H$ and $V_L$ sequences of CCL19 or CCR7 monoclonal antibodies. Once DNA or cDNA fragments encoding $V_H$ and $V_L$ segments are obtained, these DNA fragments can be further manipulated by standard recombinant DNA techniques, for example to convert the variable region genes to full-length antibody chain genes, to Fab fragment genes, or to a scFv gene. In these manipulations, a $V_L$- or $V_H$-encoding DNA fragment is operatively linked to another DNA fragment encoding another protein, such as an antibody constant region or a flexible linker. The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat et al., Sequences of Proteins of Immunological Interest, 5$^{th}$ ed., U.S. Department of Health and Human Services, NIH Publication No. 91-3242 (1991), which is hereby incorporated by reference in its entirety) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region. The sequences of human light chain constant region genes are known in the art (see e.g., Kabat et al., Sequences of Proteins of Immunological Interest, 5$^{th}$ ed., U.S. Department of Health and Human Services, NIH Publication No. 91-3242 (1991), which is hereby incorporated by reference in its entirety) and DNA fragments encompassing these regions can be obtained by standard PCR amplification. The light chain constant region can be a kappa or lambda constant region, but most preferably is a kappa constant region.

To create a scFv gene, the $V_H$- and $V_L$-encoding DNA fragments are operatively linked to another fragment encoding a flexible linker such that the $V_H$ and $V_L$ sequences can be expressed as a contiguous single-chain protein, with the $V_H$ and $V_L$ regions joined by the flexible linker (see e.g., Bird et al., "Single Chain Antigen-Binding Proteins," *Science* 242: 423-426 (1988); Huston et al., "Protein Engineering of Antibody Binding Sites: Recovery of Specific Activity in an Anti-Digoxin Single-Chain Fv Analogue Produced in *Escherichia coli,*" *Proc. Natl. Acad. Sci. USA* 85:5879-5883 (1988); McCafferty et al., "Phage Antibodies: Filamentous Phage Displaying Antibody Variable Domains," *Nature* 348:552-554 (1990), which are hereby incorporated by reference in their entirety).

Antibody mimics are also suitable therapeutic agents for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

In another embodiment of the present invention, the therapeutic agent that inhibits CCR7-CCL19 signaling thereby preventing CNS leukemia is an integrin inhibitor. Integrins are adhesion molecules that further facilitate leukocyte transendothelial cell migration by binding to their respective integrin receptor following chemotractant activation. Subsequent to the CCR7-CCL19 interaction, α4β1 (VLA-4) integrin, expressed on lymphocytes, adheres to its vascular cell adhesion molecule 1 (VCAM-1) receptor. Accordingly, in a preferred embodiment, the integrin inhibitor of the present invention is an α4β1 integrin inhibitor.

Suitable α4β1 integrin inhibitors are known in the art and include nucleic acid inhibitors, inhibitory peptides, antibodies, and small molecules. Suitable antibodies having antigenic specificity for α4β1 include monoclonal antibodies having binding specificity for the α4, e.g., Natalizumab® (Tysabri®) developed by Biogen-Idec (Cambridge, Mass.) and Elan (Dublin, Ireland), or β1 subunits, respectively. Alternatively, the small molecule dual α4 antagonist, Firategrast (GlaxoSmithKline, Brentford, Middlesex, UK), is also suitable for use in the methods of the present invention. In yet another embodiment, the α4β1 integrin inhibitor is an inhibitory peptide selected from the group consisting of an (X)CDPC peptide, an XC(Z)PC peptide, and a cyclic XCA (Z)C peptide as described by Jackson et al., "Potent α4β1 Peptide Antagonists as Potential Anti-Inflammatory Agents," *J. Med. Chem.* 40:3359-68 (1997), which is hereby incorporated by reference in its entirety, or any of the inhibitory α4β1 peptides described in U.S. Pat. No. 7,238,668 to Wayner, which is hereby incorporated by reference in its entirety.

In another embodiment of the present invention, the method of preventing central nervous system leukemia involves administering any one or more of the therapeutic agents that inhibit CCR7-CCL19 signaling described above, in combination with the subject's standard leukemia treatment regimen (e.g. chemotherapy, radiation, molecular-targeted therapeutic). In a preferred embodiment of the invention, the CCL19 inhibitor or CCR7 antagonist of the present invention is administered in combination with a Notch-1 antagonist. Because activation of the Notch-1 signaling pathway has been observed in over 80% of all T-cell acute lymphoblastic leukemia cases, a number of Notch-1 antagonists have been developed and are well known in the art. Suitable Notch-1 antagonists include without limitation gamma-secretase inhibitors selected from the group consisting of [(2S)-2-{[(3,5-Difluorophenyeacetyl]amino}-N-[(3S)1-methyl-2-oxo-5-phenyl-2,3-dihydro-1H-1,4-benzodiazepin-3-yl]propanamide] (CompE), N4N-(3,5-difluorophenacetyl)-L-alanyl]-Sphenylglycine-t-butylester (DAPT), LY411575, (5S)-(t-Butoxycarbonylamino)-6-phenyl-(4R)hydroxy-(2R) benzylhexanoyl)-L-leu-L-phe-amide (L-685,458), L-852, 647, MW167, WPE-111-31, LY450139, MRK003, R-flurbiprofen ([1,1'-Biphenyl]-4-acetic acid, 2-fluoro-alpha-methyl), NGX-555, CZC-1040, E2012, GSI-1, Begacestat (2-Thiophenesulfonamide, 5- chloro-N-[(1S)-3,3,3-trifluoro-1-(hydroxymethyl)-2-(trifluoromethyl)propyl]-), NIC5-15, BACE Inhibitor, and CHF-5074.

Alternatively, the CCL19 inhibitor or CCR7 antagonist is administered in combination with a chemotherapeutic agent. Suitable chemotherapeutic agents include without limitation cytarabine, vincristine, prednisone, daunorubicin, PEG asparaginase, methotrexate, and leucovorin.

Another aspect of the present invention is directed to a method of treating T-cell acute lymphoblastic leukemia in a subject. This method involves selecting a subject having T-cell acute lymphoblastic leukemia and administering a cocktail of chemotherapeutic agents in combination with the therapeutic agent that inhibits CCR7-CCL19 signaling under conditions effective to treat T-cell acute lymphoblastic leukemia in the selected subject.

In accordance with this aspect of the present invention, the cocktail of -20 chemotherapeutic agents includes two or more chemotherapeutic agents selected from the group consisting of cytarabine, vincristine, prednisone, daunorubicin, PEG asparaginase, methotrexate, and leucovorin.

The therapeutic inhibitor of CCR7-CCL19 signaling includes any of the nucleic acid inhibitor molecules, inhibitory peptides, antibodies, or small molecules described supra. In a preferred embodiment, the inhibitor is a human monoclonal CCL19 antibody.

Another aspect of the present invention relates to a method of treating an immune system disorder in a subject. This method involves selecting a subject having an immune system disorder and providing a therapeutic agent that inhibits CCR7-CCL19 signaling. The method further involves administering the therapeutic agent to the selected subject under conditions effective to treat the inflammatory or autoimmune condition in the selected subject.

Suitable therapeutic inhibitors of CCR7-CCL19 signaling include any one or more of the therapeutic agents described supra. In a preferred embodiment, the inhibitor is a human monoclonal CCL19 antibody.

In accordance with this aspect of the present invention, the immune system disorder is a disorder involving CCR7-CCL19 signaling. In one embodiment the immune disorder is an acute or chronic inflammatory condition. Inflammatory conditions suitable for treatment using the methods of the present invention include, without limitation, systemic anaphylaxis or hypersensitivity responses, allergies, inflammatory bowel disease, psoriasis and inflammatory dermatoses, vasculitis, spondyloarthropathy, respiratory allergic disease (e.g., asthma, allergic rhinitis and hypersensitivity lung diseases), atherosclerosis, myositis, neurodegenerative diseases, Alzheimer's disease, encephalitis, meningitis, hepatitis, nephritis, sepsis, sarcoidosis, conjunctivitis, otitis, chronic obstructive pulmonary disease, sinusitis and Behcet's syndrome.

Alternatively, the immune system disorder in accordance with this aspect of the present invention is an autoimmune condition. Autoimmune conditions suitable for treatment using this method of the present invention include, without limitation, autoimmune encephalitis, rheumatoid arthritis, juvenile rheumatoid arthritis, lupus, scleroderma, Sjogren's syndrome, Goodpasture's syndrome, Wegener's granulomatosis, polymyalgia rheumatica, Guillain-Barre syndrome, type-1 diabetes mellitus, Hashimoto's thyroiditis, Graves' disease, celiac disease, Crohn's disease, ulcerative colitis, multiple sclerosis, Addison's disease, primary biliary cirrhosis, sclerosing cholangitis, autoimmune hepatitis, and temporal arteritis.

In accordance with the methods of the present invention, the mode of administering the therapeutic agent of the present invention, including the use of suitable delivery vehicles, to a subject at risk of developing CNS leukemia, a subject having T-cell acute lymphoblastic leukemia, or a subject having an immune system disorder will vary depending on the type of therapeutic agent (e.g., nucleic acid molecule, inhibitory peptide, antibody, or small molecule).

In one embodiment, inhibitory CCL 19 or CCR7 nucleic acid molecules (i.e., antisense, siRNA, etc.), nucleic acid molecules encoding a CCL19 inhibitory peptide, or nucleic acid molecules encoding a CCL19 or CCR7 antibody or antibody binding fragment may be incorporated into a gene therapy vector to facilitate delivery.

In a preferred embodiment, the gene therapy vector carrying the inhibitory CCL19/CCR7 nucleic acid molecule, nucleic acid molecule encoding an inhibitory CCL19 peptide, or nucleic acid molecule encoding a CCL19 or CCR7 antibody or antibody binding fragment is an expression vector derived from a virus. Suitable viral vectors include, without limitation, adenovirus, adeno-associated virus, retrovirus, lentivirus, or herpes virus.

Adenoviral viral vector gene delivery vehicles can be readily prepared and utilized as described in Berkner, "Development of Adenovirus Vectors for the Expression of Heterologous Genes," *Biotechniques* 6:616-627 (1988) and Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral gene delivery vehicles can be constructed and used to deliver a gene, including a gene encoding an antibody to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179: 733-738 (1994); and Zhou et al., "Adeno-Associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable In Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver inhibitory nucleic acid molecules or nucleic acid molecules encoding a desired peptide or antibody to a target cell. One such type of retroviral vector is disclosed in U.S. Pat. No. 5,849,586 to Kriegler et al., which is hereby incorporated by reference.

Gene therapy vectors carrying the therapeutic nucleic acid molecule are administered to a subject by, for example, intravenous injection, local administration (U.S. Pat. No. 5,328,470 to Nabel et al., which is hereby incorporated by reference in its entirety) or by stereotactic injection (see e.g., Chen et al. "Gene Therapy for Brain Tumors: Regression of Experimental Gliomas by Adenovirus Mediated Gene Transfer In Vivo," *Proc. Nat'l. Acad. Sci, USA* 91:3054-3057 (1994), which is hereby incorporated by reference in its entirety). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. Gene therapy vectors typically utilize constitutive regulatory elements which are responsive to endogenous transcriptions factors.

Another suitable approach for the delivery of the therapeutic agents of the present invention, including the inhibitory nucleic acid molecules, the nucleic acid molecules encoding an inhibitory CCL 19 peptide or the inhibitory peptide itself, and the nucleic acid molecules encoding the CCL19 or CCR7 antibody or the antibodies themselves, involves the use of liposome delivery vehicles.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated therapeutic agent at the primary target site. This can be accomplished, for example, in a passive manner where the liposome bilayer degrades over time through the action of various agents in the body.

In contrast to passive drug release, active drug release using liposome delivery vehicles can also be achieved. For example, liposome membranes can be constructed to be pH sensitive (see e.g., Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987), which is hereby incorporated by reference in its entirety). When liposomes are endocytosed by a target cell, for example, they can be routed to acidic endosomes which will destabilize the liposome and result in drug release. Alternatively, the liposome membrane can be chemically modified such that an enzyme placed as a coating on the membrane slowly destabilizes the liposome.

Different types of liposomes can be prepared using methods known in the art, see e.g., Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

Yet another approach for delivery of an inhibitory CCL19 peptide involves the conjugation of the desired peptide or polypeptide to a stabilized polymer to avoid enzymatic degradation of the inhibitory peptide. Conjugated peptides or polypeptides of this type are described in U.S. Pat. No. 5,681,811 to Ekwuribe, which is hereby incorporated by reference in its entirety.

The therapeutic agents of the present invention can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, intranasal drops). Typically, parenteral administration is the preferred mode of administration.

Therapeutic agents of the present invention are formulated in accordance with their mode of administration. For oral administration, for example, the therapeutic agents of the present invention are formulated into an inert diluent or an assimilable edible carrier, enclosed in hard or soft shell capsules, compressed into tablets, or incorporated directly into food. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits inhibition of proteolysis and uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, "Soluble Polymer-Enzyme Adducts," In: *Enzymes as Drugs*, Hocenberg and Roberts, eds., Wiley-Interscience (1981), which is hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucrulose, or saccharin. When the dosage unit form is a capsule, it may contain, in addition to materials of the above type, a liquid carrier such as a fatty oil.

The therapeutic agents of the present invention may also be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the therapeutic agents of the present invention, for the prevention of CNS leukemia, the treatment of T-cell acute lymphoblastic leukemia, and/or the treatment of an immune system disorder vary depending upon many different factors, including type and stage of leukemia or immune system disorder, mode of administration, target site, physiological state of the patient, other medications or therapies administered, and physical state of the patient relative to other medical complications. Treatment dosages need to be titrated to optimize safety and efficacy.

The CCL19 and CCR7 antibodies of the present invention can be administered in a single dose or multiple doses. The dosage can be determined by methods known in the art and can be dependent, for example, upon the individual's age, sensitivity, tolerance and overall well-being. Suitable dosages for antibodies can be from about 0.1 mg/kg body weight to about 10.0 mg/kg body weight per treatment.

The therapeutic agents of the present invention can be administered to an individual (e.g., a human) alone or in conjunction with one or more other therapeutic agents of the invention. As described supra, when the therapeutic agent of the present invention is administered to an individual having leukemia to prevent the onset of CNS leukemia, the therapeutic agent can be administered in conjunction with one or more chemotherapeutic agents, Notch-1 inhibitors, or other therapeutic agents administered for the treatment of leukemia.

When the therapeutic agent of the present invention is administered to an individual suffering from an acute or chronic inflammatory condition, the therapeutic agent may be given in conjunction with an anti-inflammatory or analgesic agent such as an opiate agonist, a lipoxygenase inhibitor, a cyclooxygenase inhibitor, an interleukin inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example acetaminophen, aspirin, codiene, fentanyl, ibuprofen, indomethacin, ketorolac, morphine, naproxen, phenacetin, piroxicam, a steroidal analgesic, sufentanyl, sunlindac, tenidap. Likewise, when the therapeutic agent of the present invention is administered to an individual having an autoimmune disease, the therapeutic agent can be administered in conjunction with standard treatment of care for the particular autoimmune disorder.

Another aspect of the present invention is directed to a method of identifying a compound capable of preventing leukocyte transendothelial cell migration. This method involves providing one or more candidate compounds and contacting the one or more candidate compounds with a CCR7-CCL19 signaling system. The method further involves determining whether the one or more candidate compounds inhibit CCR7-CCL19 mediated signaling and identifying one or more candidate compounds that inhibit CCR7-CCL19 mediated signaling as a suitable compound for preventing leukocyte transendothelial cell migration.

In accordance with this aspect of the present invention, the CCR7-CCL19 signaling system includes any biological (cell, tissue, or whole animal) experimental system which affords detection of the CCR7-CCL19 binding interaction or CCR7-CCL19 signaling pathway. The binding interaction between CCL19 and CCR7 initiates the process of transendothelial cell migration or diapedesis. Assays for assessing a candidate compounds ability to disrupt the direct binding interaction of CCL19 and CCR7 include any well known in vitro binding assay, such as a receptor binding assay (RBA), enzyme-linked immunoabsorbent assay (ELISA), a co-immunoprecipitation assay, or a fluorescence resonance energy transfer (FRET) assay. CCR7-CCL19 signaling can also be measured using a functional assay, for example, a standard in vitro leukocyte-endothelial cell adhesion assay or leukocyte transendothelial migration assay. In a leukocyte-endothelial cell adhesion assay, such as that described in Jeanne-Marie Kiely et al., *Leukocyte-Endothelial Monolayer Adhesion Assay (Static Conditions)*, in ADHESION PROTEIN PROTOCOLS 131-136 (E. Dehana & M. Corada eds., 1999), which is hereby incorporated by reference in its entirety, a candidate compound capable of preventing leukocyte transendothelial cell migration is a compound that inhibits CCR7-CCL19 mediated leukocyte cellular adhesion to endothelial cells. Likewise, using an endothelial cell migration assay, such as the 96-well format transendothelial migration assay available from Millipore (Billerica, Mass.), compounds that prevent CCR7-positive leukocyte transendothelial cell migration can be readily identified.

Compounds capable of preventing leukocyte transendothelial cell migration can also be identified using an in vivo CCR7-CCL19 signaling system. A preferred in vivo CCR7-CCL19 signaling system adapted to detecting the development of central nervous system leukemia via CCR7 expressing leukemic cell transendothelial cell migration is described infra in the examples. In this model, labeled T-ALL cell lines expressing the CCR7 receptor are transplanted into a suitable recipient animal (e.g., Rag2$^{-/-}$γc$^{-/-}$ mouse). Following transplantation, one or more recipient animals are administered a candidate compound or a control (placebo) compound, and the migration of CCR7 leukemic cells is monitored using bioluminescent imaging. If the recipient animals receiving the candidate compound have a reduction in CCR7 positive cell CNS infiltration compared to recipient animals receiving control compounds, the candidate compound is one that is capable of preventing leukocyte transendothelial cell migration and capable of preventing central nervous system leukemia.

In accordance with this aspect of the present invention suitable candidate compounds capable of preventing leukocyte transendothelial cell migration include, but are not limited to, inhibitory CCL19 peptides, small molecule CCR7 antagonists, and antibodies directed to CCL19 or CCR7.

Candidate compounds that are identified as capable of preventing CCR7-CCL19 leukocyte transendothelial cell migration are suitable compounds for administration to a subject at risk for developing or having developed central nervous system leukemia, a subject having T-cell acute lymphoblastic leukemia, or a subject having an immune disorder in accordance with the methods of the present invention described supra.

EXAMPLES

The following examples illustrate various methods for compositions in the treatment method of the invention. The examples are intended to illustrate, but in no way limit, the scope of the invention.

Example 1

Animals

C57BL/6 and Rag2$^{-/-}$γc$^{-/-}$ mice were purchased from Jackson Laboratories and Taconic Farms. CCR7-knockout (KO) and plt mice lacking CCL19 expression have been described previously (Forster et al., "CCR7 Coordinates the Primary Immune Response by Establishing Functional Microenvironments in Secondary Lymphoid Organs," *Cell* 99:23-33 (1999) and Gunn et al., "Mice Lacking Expression of Secondary Lymphoid Organ Chemokine Have Defects in Lymphocyte Homing and Dendritic Cell Localization," *J Exp Med* 189:451-60 (1999), which are hereby incorporated by reference in their entirety). All mice were kept in specific pathogen-free animal facilities. All animal procedures were performed in accordance to the guidelines of the Institutional Animal Care and Use Committee of the New York University School of Medicine.

Example 2

Recombinant DNA Constructs and Retrovirus Production and Infection

The retroviral plasmid containing Notch-1 (N1-IC), its parent CMMP-based vector (Sicinska et al., "Requirement for Cyclin D3 in Lymphocyte Development and T-Cell Leukemias," *Cancer Cell* 4:451-61 (2003), which is hereby incorporated by reference in its entirety), the pMXs IRES-mCherry retroviral vector and the pWPI lentivirus (a gift from Eva Hernando) were used in the studies described infra. Viral supernatants were generated as described previously (Ory et al., "A Stable Human-Derived Packaging Cell Line for Production of High Titer Retrovirus/Vesicular Stomatitis Virus G Pseudotypes," *Proc Natl Acad Sci USA* 93: 11400-6 (1996), which is hereby incorporated by reference in its entirety).

Isolation, retroviral infection and reconstitution experiments were performed as previously described (Sicinska et al., "Requirement for Cyclin D3 in Lymphocyte Development and T-Cell Leukemias," *Cancer Cell* 4:451-61 (2003), which is hereby incorporated by reference in its entirety).

Example 3

Antibodies and Reagents

Mouse CD4-APC, CD8-PE-Cy7, CCR7-PE, B220, and CD31 and human CCR7-PE and CD3-APC primary antibodies were purchased from BD Bioscience (San Jose, Calif.). Human CD3 antibody was obtained by DAKO (Carpinteria, Calif.). Mouse CCL19 and CCL21 were procured from R&D (Minneapolis, Minn.). Mouse CD31 was obtained from Pharmingen. Cytokines and chemokines were obtained from Peprotech (Rochy Hill, N.J.). Secondary antibodies were purchased from Jackson Laboratories (West Grove, Pa.). Immunohistochemical analysis was performed using standard methods as described previously (Vilimas et al., "Targeting the NF-KappaB Signaling Pathway in Notch 1-Induced T-Cell Leukemia," *Nat Med* 13:70-7 (2007), which is hereby incorporated by reference in its entirety).

Example 4

Chemotaxis Assays

Chemotaxis assays were performed as previously described by Scimone et al., "A Multistep Adhesion Cascade for Lymphoid Progenitor Cell Homing to the Thymus," *Proc Natl Acad Sci U.S.A.* 103:7006-11 (2006), which is hereby incorporated by reference in its entirety.

Example 5

Quantitative RT-PCR

RNA was isolated using RNeasy Plus Mini Kit (Qiagen, Valencia, Calif.) columns and used to synthesize cDNA with the SuperScript First-Strand Kit (Invitrogen, Carlsbad, Calif.). Real time PCR was performed using iQ SYBR Green Supermix and an iCycler (Bio-Rad, Hercules, Calif.). Relative expression was determined from cycle threshold ($C_T$) values and was normalized using β-actin as an internal control.

Example 6

Bioluminescent Imaging

Imaging of luciferase-tagged leukemic cells were performed as previously described by Tseng et al., "Tumor-Specific In Vivo Transfection with HSV-1 Thymidine Kinase Gene Using a Sindbis Viral Vector as a Basis for Prodrug Ganciclovir Activation and PET," *J Nucl Med* 47:1136-43 (2006), which is hereby incorporated by reference in its entirety.

Example 7

Intravital Microscopy

2-Photon imaging was performed as previously described by Shakhar et al., "Stable T-Cell-Dendritic Cell Interactions Precede the Development of Both Tolerance and Immunity In Vivo," *Nat Immunol* 6:707-14 (2005), which is hereby incorporated by reference in its entirety. Individual cell tracing and data analysis was performed as previously described (Mempel et al., "T-Cell Priming by Dendritic Cells in Lymph Nodes Occurs in Three Distinct Phases," *Nature* 427:154-9 (2004), which is hereby incorporated by reference in its entirety).

Example 8

Micro-Array Analysis

The accession numbers for the individual array comparisons are Gene Expression Omnibus (GEO) series GSE6396, samples GSM 147443, GSM 147464, and GSM147508. Sample preparation and processing is detailed in Vilimas et al., "Targeting the NF-KappaB Signaling Pathway in Notch1-Induced T-Cell Leukemia," *Nat Med* 13:70-7 (2007), which is hereby incorporated by reference in its entirety. Pathway analysis of the micro-array mRNA profiling results was performed using the Gene Ontology and KEGG pathway mapping within the web-based tool Database for Annotation, Visualization and Integrated Discovery (DAVID). The results of category/pathway enrichment were manually curated for focused contents based on gene number and associated p-value, and are summarized in Table 1 (below) which lists Gene Ontology and KEGG Pathway categories significantly enriched for specific gene effectors with candidate roles for the infiltration of leukemic cells in the CNS.

TABLE 1

Gene Ontology and KEGG Pathway categories significantly enriched for specific gene effectors with candidate roles for the infiltration of leukemic cells in the CNS.

| CATEGORY TYPE | CATEGORY | CATEGORY ID | GENE # | GENE SYMBOL |
|---|---|---|---|---|
| UP | GOTERM_BP | Lymphocyte activation | GO: 0046649 | 26 | Lag3, Tgfb1, Ap3b1, Il12b, Efnb1, Gadd45g, H2-DMa, Cd1d1, Egr1, Syk, Cbfb, Itgax, Tpd52, Lst1, Ms4a1, Relb, Nbn, H2-Oa, Il4, Ptprc, Casp3, Il2rg, Spp1, Il18, Icosl, Cd3g |
| | GOTERM_BP | Cell-cell adhesion | GO: 0016337 | 4 | Cdh1, Adam8, Icam2, Cd164 |
| | GOTERM_BP | Chemotaxis | GO: 0006935 | 2 | Spp1, Lsp1 |
| DOWN | GOTERM_BP | Cell adhesion | GO: 0007155 | 21 | Cd84, Tsc2, Cd97, Faf1, Pscd2, Celsr1, Lmo4, Pstpip1, Csf3r, Pnn, Itgam, Zyx, Itgb2l, Lgals1, Tgfbi, Spn, Cd24a, Bcl10, Mag, B4galt1, Sell |
| | GOTERM_BP | Chemotaxis | GO: 0006935 | 11 | Tsc2, Il16, Plp2, Itgam, Fcgr3, S100a8, Lect2, Mapk14, S100a9, Csf3r, Fpr1 |
| | GOTERM_BP | Leukocyte migration | GO: 0050900 | 7 | Il16, Itgam, Fcgr3, Cd24a, B4galt1, S100a9, Csf3r |

TABLE 1-continued

Gene Ontology and KEGG Pathway categories significantly enriched for specific gene effectors with candidate roles for the infiltration of leukemic cells in the CNS.

| CATEGORY TYPE | CATEGORY | CATEGORY | CATEGORY ID | GENE # | GENE SYMBOL |
|---|---|---|---|---|---|
| UP | GOTERM_CC | Extracellular matrix | GO: 0031012 | 11 | Mmp13, Mmp9, Wnt4, Tgfb1, Entpd1, Spp1, Col4a2, Wnt11, Gpc3, Tgm2, Mmp14 |
|  | GOTERM_CC | Integrin complex | GO: 0008305 | 7 | Itgax, Itgb1, Itga3, Itga2b, Itgb5, Itgae, Itgb7 |
|  | GOTERM_CC | Actin cytoskeleton | GO: 0015629 | 7 | My010, Clic4, Aif1, Wdr1, Gabarap, Actg2, Tnni2 |
|  | GOTERM_CC | Cell-matrix junction | GO: 0030055 | 5 | Ptprc, Ilk, Itga2b, Limk1, Evl |
| DOWN | GOTERM_CC | Cell junction | GO: 0030054 | 6 | Nphp1, Gria3, Zyx, Rapsn, Grin2d, Pnn |
|  | GOTERM_CC | Extracellular matrix | GO: 0031012 | 5 | Adam15, Gpc1, Bgn, Tgfbi, Spn |
|  | GOTERM_CC | Integrin complex | GO: 0008305 | 2 | Itgam, Itgb2l |
| UP | GOTERM_MF | Integrin binding | GO: 0005178 | 5 | Spp1, Syk, Itgb1, Itgb5, Nisch |
|  | KEGG | Cell adhesin molecules (CAMs) | mmu04514 | 19 | H2-EB1, H2-Ea, Cd6, Itgb1, H2-T23, H2-Ab1, H2-Oa, H2-Q1, H2-T22, Cdh1, Ptprc, Cd22, H2-DMa, H2-DMb1, Cd86, Icosl, Itgb7, H2-Q7, Icam2 |
|  | KEGG | Focal adhesion | mmu04510 | 17 | Birc3, Col4a2, Itgb1, Grb2, Pdgfa, Itgb5, Pdgfrb, Ilk, Hras1, Met, Map2k1, Birc2, Spp1, Itga2b, Itga3, Jun, Itgb7 |
|  | KEGG | Regulation of actin cytoskeleton | mmu04810 | 13 | Itgax, Rras, Itgb1, Pdgfa, Itgb5, Pdgfrb, Map2k1, Hras1, Itga2b, Itga3, Limk1, Itgb7, Itgae |
|  | KEGG | ECM-receptor interaction | mmu04512 | 8 | Gp1ba, Spp1, Col4a2, Itgb1, Itga3, Itga2b, Itgb5, Itgb7 |
|  | KEGG | Gap junction | mmu04540 | 7 | Hras1, Map2k1, Adcy6, Grb2, Pdgfa, Adcy7, Pdgfrb |
| DOWN | KEGG | Regulation of actin cytoskeleton | mmu04810 | 8 | Pip5k1a, Apc, Itgam, Diap2, Sos2, Itgb21, Tiam1, Mapk1 |
|  | KEGG | Gap junction | mmu04540 | 5 | Itpr1, Sos2, Tuba8, Mapk1, Adcy9 |
|  | KEGG | Cell adhesion molecules (CAMs) | mmu04514 | 5 | Itgam, Itgb21, Spn, Mag, Sell |
|  | KEGG | Leukocyte transendothelial migration | mmu04670 | 3 | Itgam, Itgb21, Mapk14 |

GOTERM_BP = Gene Ontology Biological Process; GOTERM_CC = Gene Ontology Cellular Compartment; GOTERM_M = Gene Ontology Molecular Function; KEGG = Kyoto Encyclopedia of Genes and Genomes. The GO and KEGG pathway analysis was performed as described in the Method Section. UP indicates functional categories based on increased mRNA abundance, and DOWN categories based on decreased mRNA abundance.

Example 9

CCR7-CCL19 Signaling Regulation of Leukemic T-Cell CNS Infiltration

Recent studies have identified that mutations of the developmental regulator Notch 1, can be identified in the majority of T-ALL patients (Weng et al., "Activating Mutations of NOTCH 1 in Human T-Cell Acute Lymphoblastic Leukemia," Science 306:269-71 (2004), which is hereby incorporated by reference in its entirety). It is estimated that activation of the Notch1 signaling pathway is found in at least 80% of all T-ALL cases (Weng et al., "Activating Mutations of NOTCH 1 in Human T-Cell Acute Lymphoblastic Leukemia," Science 306:269-71 (2004); Thompson et al., "The SCFFBW7 Ubiquitin Ligase Complex as a Tumor Suppressor in T-Cell Leukemia," J Exp Med 204:1825-35 (2007); Palomero et al., "Mutational Loss of PTEN Induces Resistance to NOTCH 1 Inhibition in T-Cell Leukemia," Nat Med 13:1203-10 (2007); O'Neil et al., "FBW7 Mutations in Leukemic Cells Mediate NOTCH Pathway Activation and Resistance to Gamma-Secretase Inhibitors," J Exp Med 204:1813-24 (2007), which are hereby incorporated by reference in their entirety). To investigate the mechanisms of T-ALL CNS infiltration and derive information that could be useful for treatment, animal models involving expression of oncogenic Notch 1 (N1-IC) were established. The first model entails transplantation of wild-type (WT) hematopoietic progenitor cells carrying N1-IC introduced by retroviral transfer (WT$^{N1-IC}$) (Vilimas et al., "Targeting the NF-KappaB Signaling Pathway in Notch 1-Induced T-Cell Leukemia," Nat Med 13:70-7 (2007), which is hereby incorporated by reference in its entirety). The second model is based on cre/loxP recombination and involves Mx-cre mice crossed with partners carrying dormant transgenic N1-IC which was knocked-in into the ubiquitously expressed Eef1a1 locus (Klinakis et al., "Igf1r as a Therapeutic Target in a Mouse Model of Basal-Like Breast Cancer," Proc Natl Acad Sci U.S.A. 106(7):2359-64 (2009), which is hereby incorporated by reference in its entirety). The dormant N1-IC exerts oncogenic action after excision of a DNA segment blocking its expression when cre is expressed specifically in hematopoietic progenitor cells by the IFNa-inducible Mx1 promoter upon polyl:polyC injection.

Figure 1C:
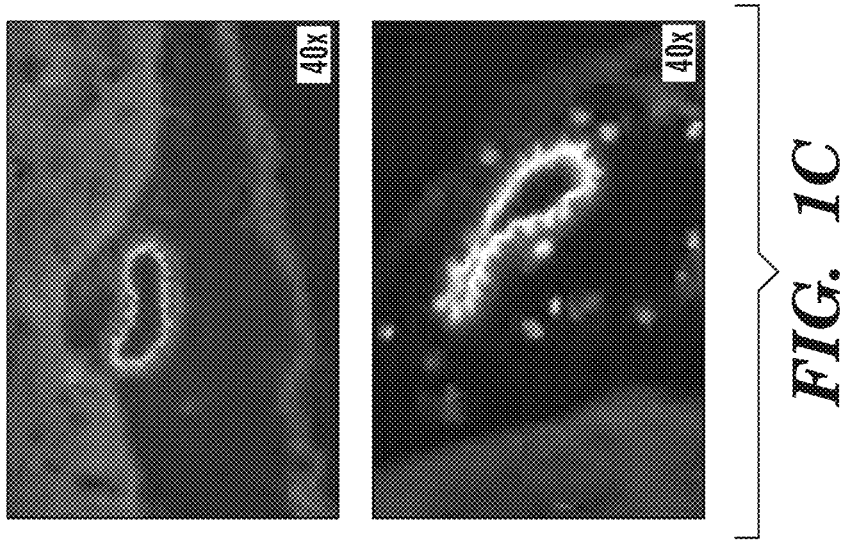
Figure 1B:
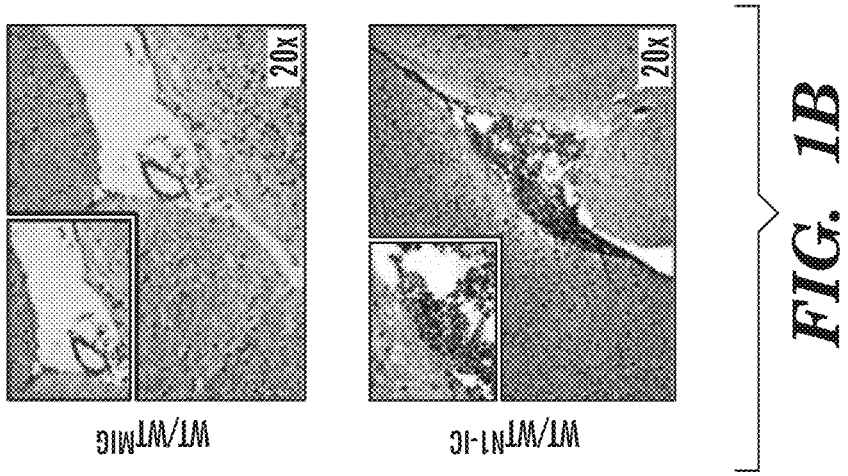
Figure 7A:
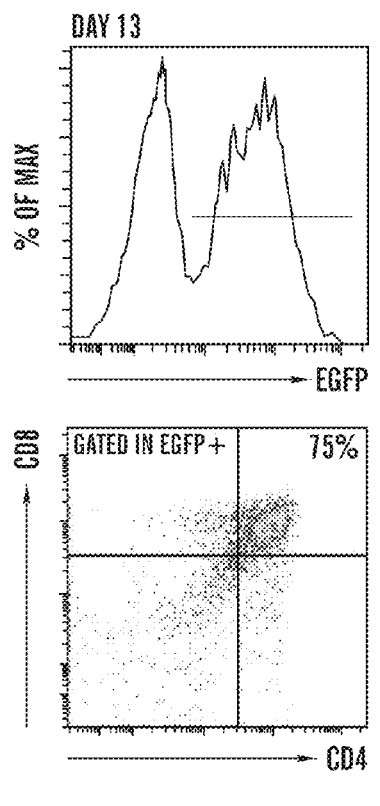
FIGS. 7A-7C illustrate the progressive appearance of CNS-infiltrating leukemic cells. The presence of CD4+CD8+ N1-IC/EGFP+ cells were observed in peripheral blood (FIG. 7A), but not the leptomeningeal spaces of the brain (FIG. 7B) of WT/WT$^{N1-IC}$ transplanted animals 13 days post transfer.
Figure 7B:
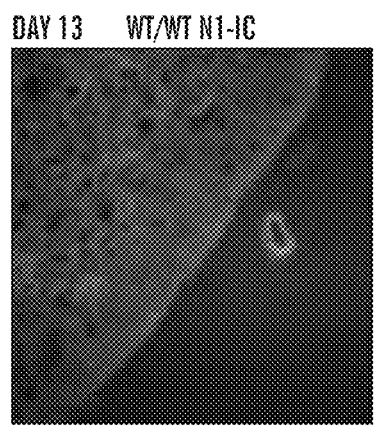
Figure 7C:
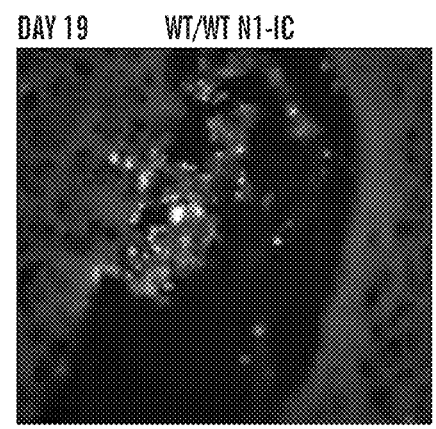

Both models develop T-ALL, presenting atypical CD4+8+ T-cells in peripheral blood samples as well as other characteristic pathological features of T-ALL (FIGS. 1A-1C, FIG. 5A, and FIGS. 6A-6H). Immunohistochemical analysis demonstrated that in both models, N1-IC/EGFP+ and CD3+ leukemic cells efficiently infiltrate the leptomeningeal spaces of the recipient animal's brain (FIGS. 1B-1C and FIG. 5B). Further studies showed that the CNS infiltration was progressive and was initially detected in mice in which leukemic blasts were readily detected in their peripheral blood (FIGS. 7A-7C) and secondary lymphoid tissue. Thus oncogenic N1-IC expression was able to induce T-ALL and target the transformed cells to the CNS.

Figure 2A:
FIGS. 2A-2D show that CCR7 expression and response to CCL19/21 is induced by Notch1 activation.
Figure 2C:
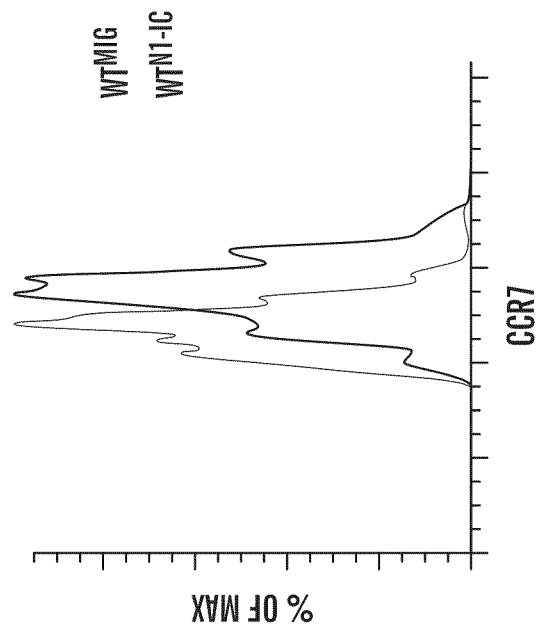
Figure 2B:
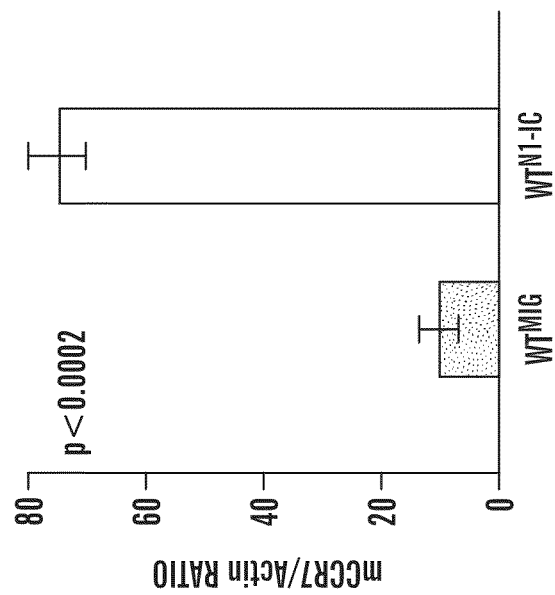
Figure 2D:
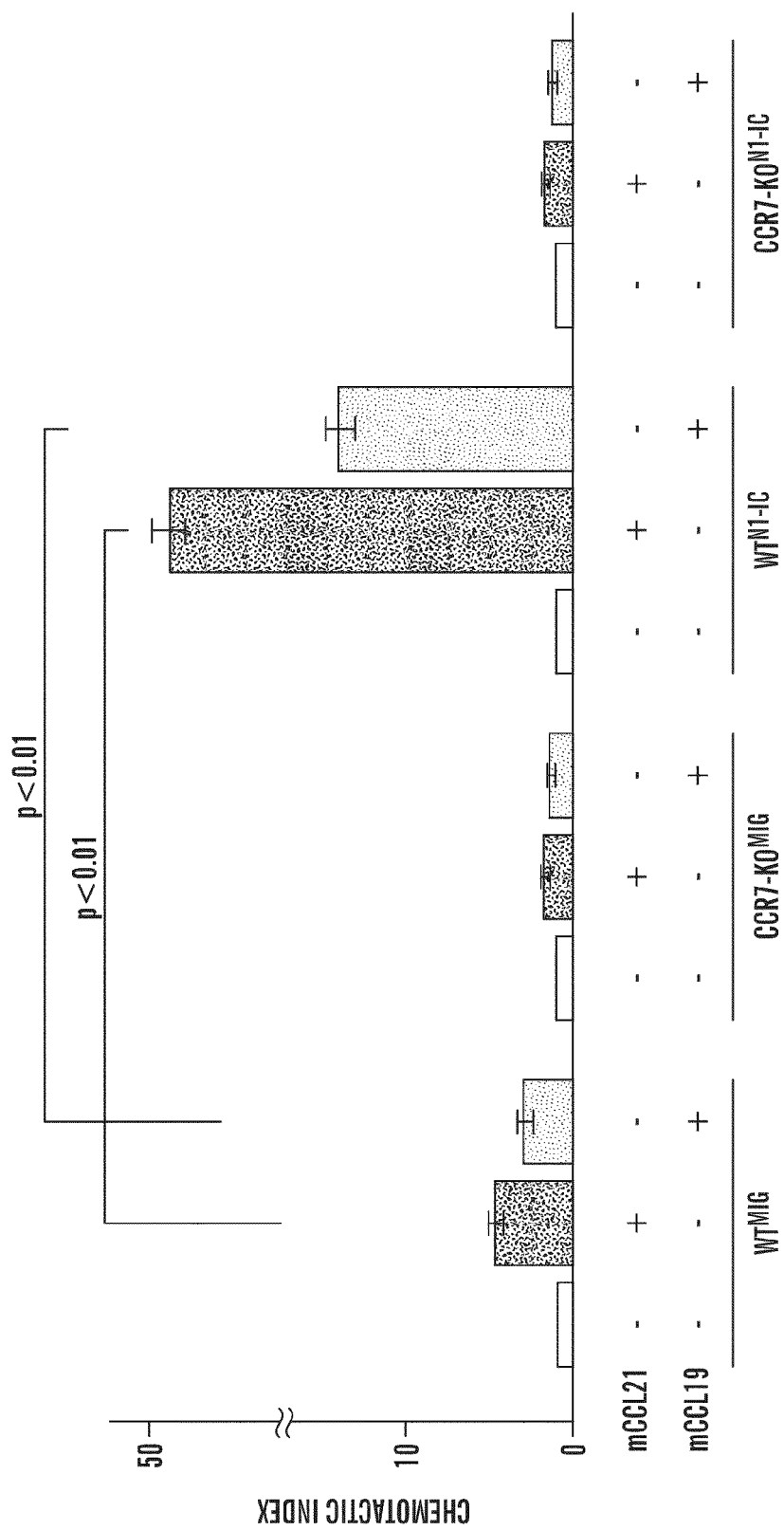

A genome-wide transcriptome approach was employed to identify Notch 1-induced adhesion regulators that could be essential for CNS infiltration. Uncommitted hematopoietic progenitors were infected with N1-IC/EGFP+ retroviruses and gene expression was recorded 48 h later (Vilimas et al., "Targeting the NF-KappaB Signaling Pathway in Notch 1-Induced T-Cell Leukemia," Nat Med 13:70-7 (2007), which is hereby incorporated by reference in its entirety). Detailed data mining demonstrated that a considerable fraction of Notch-controlled genes are potential regulators of cell adhesion, migration and metastasis (FIG. 2A and Table 1). The expression of a specific gene, the chemokine receptor CCR7 was significantly upregulated (FIG. 2A), and its expression remained constant after several days of culture. CCR7 over-expression and function was also confirmed by real time PCR (FIG. 2B), flow cytometry analysis (FIG. 2C), and in vitro chemotaxis assays toward its known ligands CCL19 and CCL21 (FIG. 2D). CCR7 is a very attractive candidate for mediating CNS leukemic cell infiltration as it is a known regulator of lymphocyte migration and has been suggested to be important for the trafficking of lymphocytes participating in CNS immunosurveillance (Charo et al., "The Many Roles of Chemokines and Chemokine Receptors in Inflammation," *N Engl J Med* 354:610-21 (2006) and Cardona et al., "Chemokines In and Out of the Central Nervous System: Much More Than Chemotaxis and Inflammation," *J Leukoc Biol* 84(3):587-94 (2008), which are hereby incorporated by reference in their entirety). CCR7 functions through its interaction with two main chemokine ligands, CCL19 and CCL21 (Forster et al., "CCR7 and its Ligands: Balancing Immunity and Tolerance," *Nat Rev Immunol* 8:362-71 (2008), which is hereby incorporated by reference in its entirety). Both CCR7 and CCL19/21 expression and function have been involved in the directional metastasis of several types of solid tumors, including melanomas and breast cancers (Muller et al., "Involvement of Chemokine Receptors in Breast Cancer Metastasis," *Nature* 410:50-6 (2001) and Shields et al., "Autologous Chemotaxis as a Mechanism of Tumor Cell Homing to Lymphatics via Interstitial Flow and Autocrine CCR7 Signaling," *Cancer Cell* 11:526-38 (2007), which are hereby incorporated by reference in their entirety).

Figure 3A:
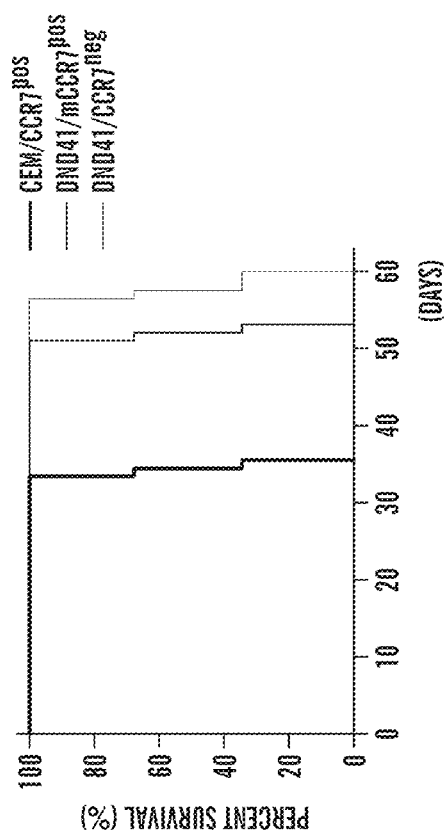
FIGS. 3A-3D show that CCR7 expression is sufficient for CNS infiltration of human T-ALL cells.
Figure 3B:
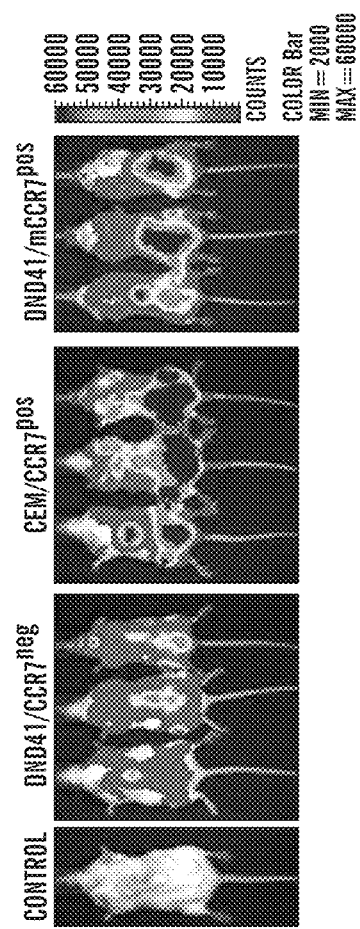
Figure 3C:
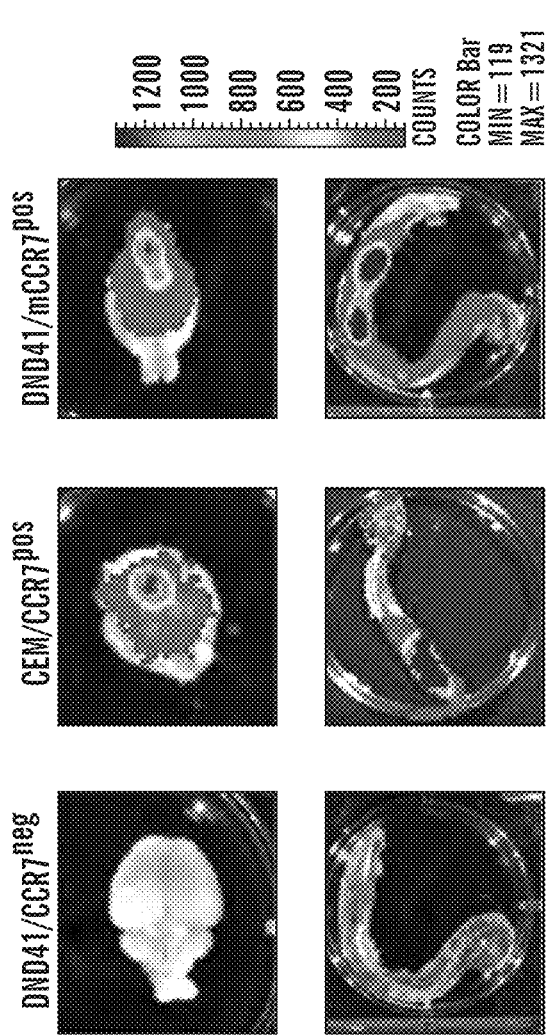
Figure 3D:
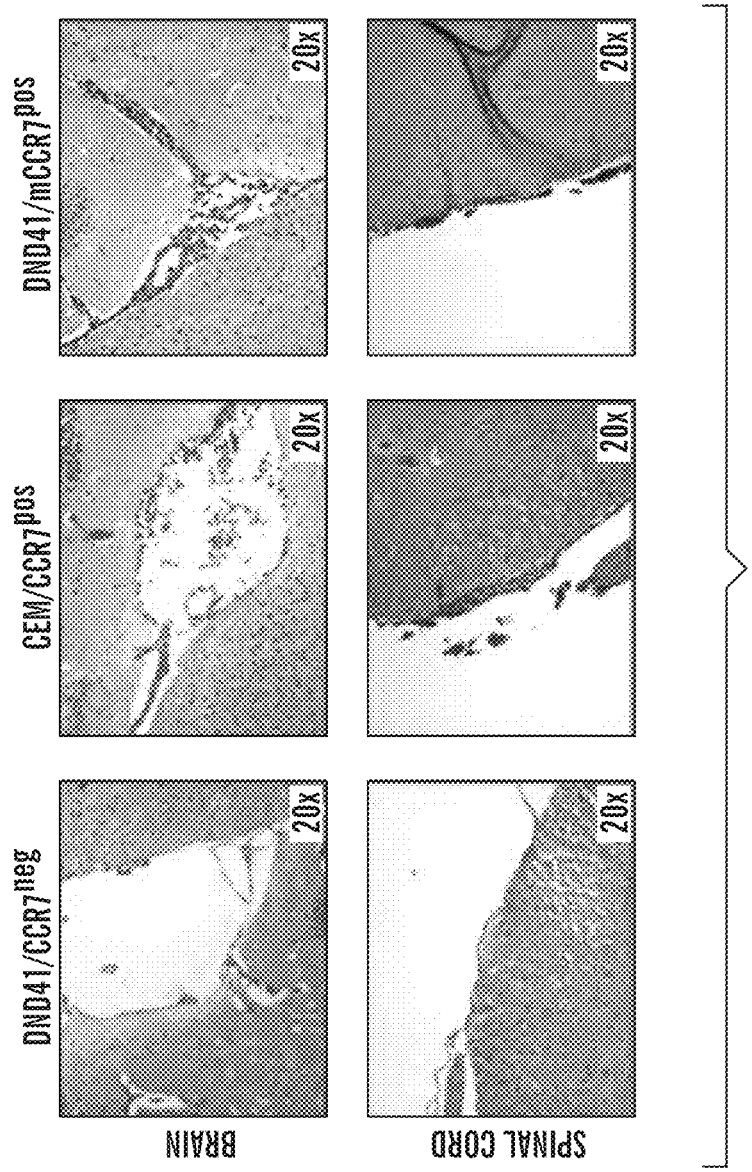
Figure 8A:
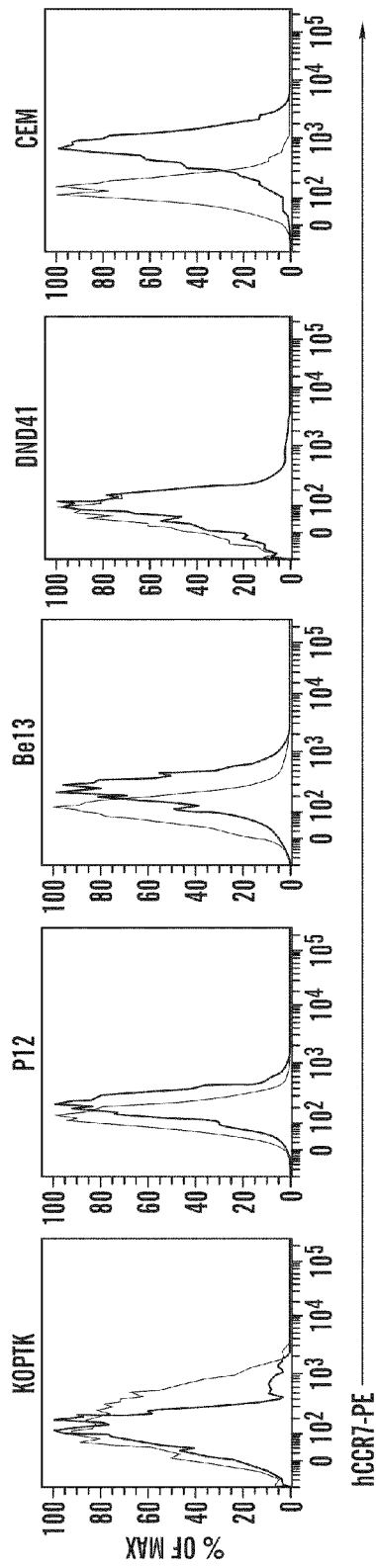
FIGS. 8A-8B are histograms showing CCR7 expression in T-ALL cell lines and human primary T-ALL cells. Expression of CCR7 protein was observed on the surface of T-ALL cell lines (FIG. 8A) and primary T-ALL cells (FIG. 8B; see e.g., #114, #358, and #479). Non-leukemic control cells (i.e., #846, #281) are also shown in FIG. 8B. Peripheral blood cells gated on CD3 positive cells.
Figure 8B:
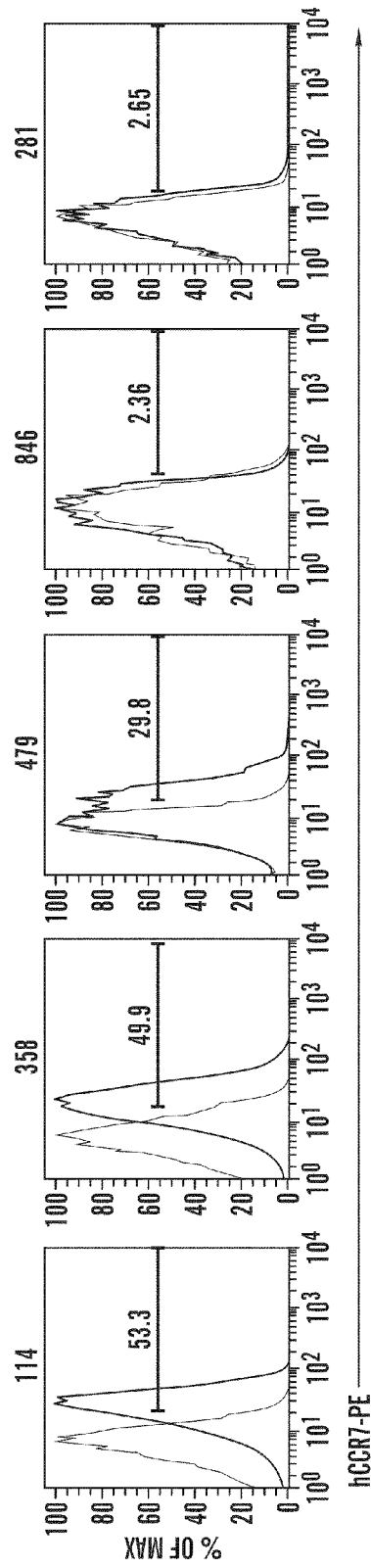
Figure 9C:
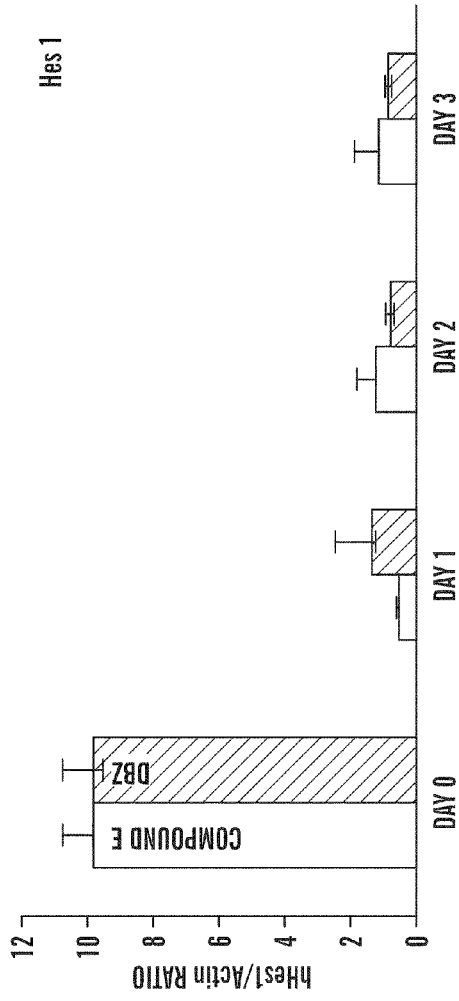
Figure 9D:
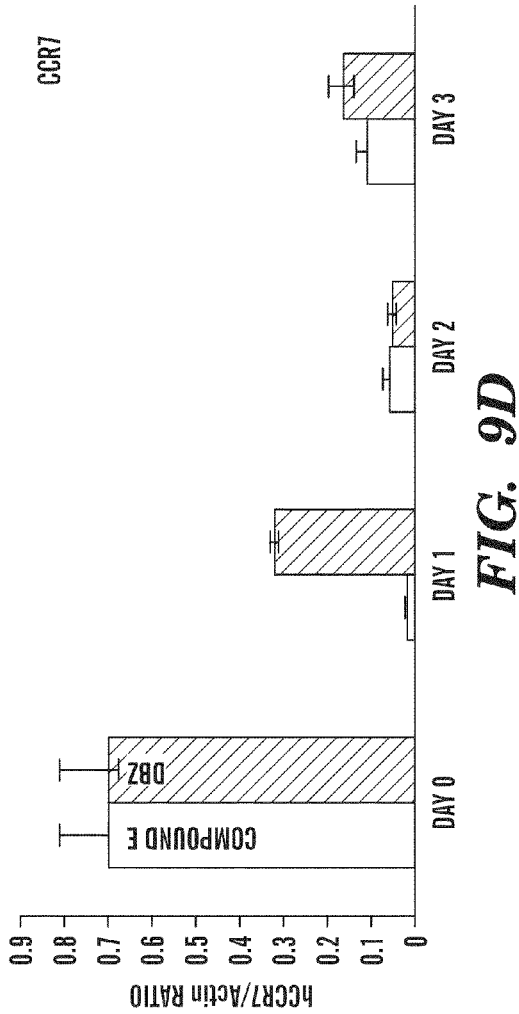

To further correlate Notch 1 activation and CCR7 expression, T-ALL cell lines harboring Notch 1 activating mutations and primary T-ALL samples were analyzed. Strikingly, surface CCR7 was expressed in 80% (4/5) of T-ALL lines (FIG. 8A) and in 73% (8/11) of peripheral blood from primary T-ALL samples (FIG. 8B; #114, #358, and #479). CCR7 expression in the T-ALL cell lines was dependent on Notch 1 activation, as repression of Notch 1 processing due to the addition of γ-secretase inhibitors (DBZ or Compound E) lead to significant down-regulation of CCR7 mRNA and protein expression (FIG. 9D). To obtain a preliminary estimate of the importance of CCR7 expression in CNS infiltration, two human T-ALL lines were selected (FIG. 8A), one expressing CCR7 (CEM/CCR7$^{pos}$) and one deficient in CCR7 expression (DND41/CCR7$^{neg}$). Both cell lines were infected using a luciferase-expressing lentivirus. To study disease induction and progression, the cells were transplanted into lymphoid Rag2−/− γc−/− host animals. Transplantation of an identical number of leukemia cells led to distinct survival patterns as host animals which received CEM/CCR7$^{pos}$ cells succumbed to the leukemic disease earlier that the ones receiving the DND41/CCR7$^{neg}$ cells (FIG. 3A). Using live animal bioluminescent imaging, a higher tumor load in mice that received the CEM/CCR7$^{neg}$ cell line was observed (FIG. 3B). Most importantly, the brain and spinal cord of CEM/CCR7$^{pos}$-transplanted hosts (but not the DND41/CCR7$^{neg}$) were infiltrated by T-ALL cells (FIG. 3C). Further histopathological analysis confirmed the localization of the infiltrating cells in leptomeningeal spaces (FIG. 3D).

Figure 10B:
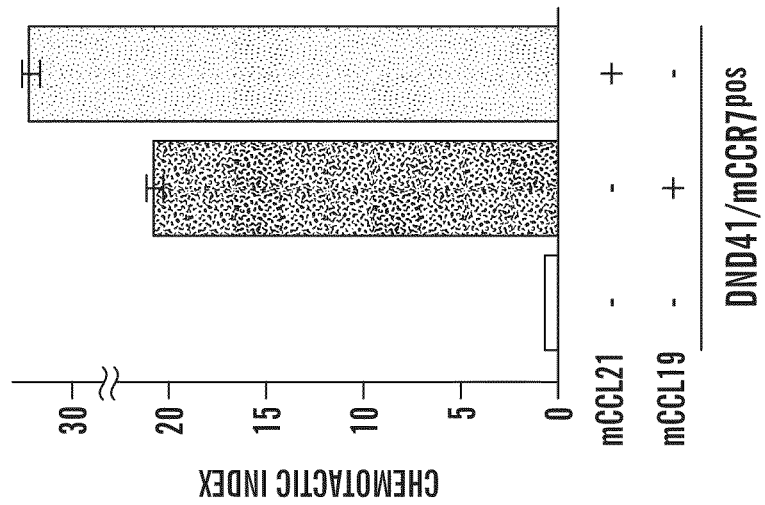
FIGS. 10A-10B show that ectopic expression of CCR7 restores cellular chemotactic response to CCL19/21. Infection of DND41/CCR7$^{neg}$ cells with a mCCR7-mCherry retrovirus (DND41/mCCR7$^{pos}$) leads to the surface expression of the CCR7 receptor (FIG. 10A). Ectopic CCR7 expression leads to enhanced chemotaxis of the DND41 cells towards CCL19/21 (FIG. 10B). Error bars define standard deviation from mean.
Figure 10A:
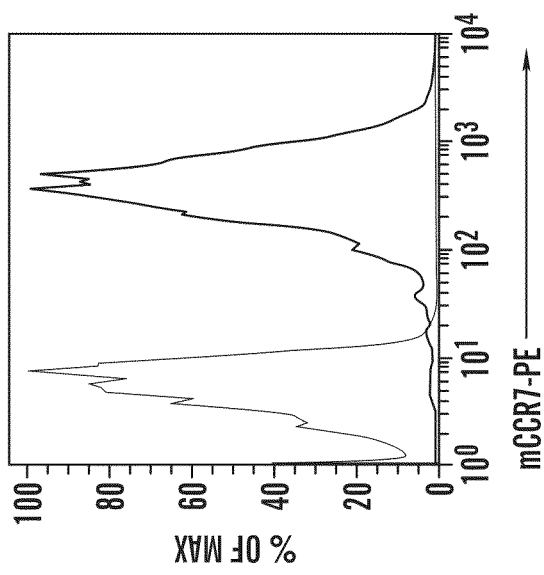

As a next step, the sufficiency of CCR7 over-expression for the recruitment of leukemic T-cells in the CNS was addressed. Mouse CCR7 (mCCR7) in the DND41/CCR7$^{neg}$ human T-ALL cell line was expressed using a bicistronic retroviral vector expressing CCR7 in conjunction with the expression of the mCherry fluorochrome (FIG. 10A). Retroviral transduction induced mCherry and mCCR7 expression and mCherry$^{pos}$/DND41/mCCR7$^{pos}$ (DND41/mCCR7$^{pos}$) cells acquired the ability to efficiently respond to both CCL19 and CCL21 (FIG. 10B). Infected cells and control cells (i.e., mCherry-only expressing cells) were injected in Rag2−/− γc−/− hosts. All recipients developed T-ALL (FIGS. 3A-3B) but no CNS infiltration was detected in mice transplanted with control DND41/CCR7$^{neg}$ cells (FIG. 3C). On the other hand, CCR7 ectopic expression was sufficient to allow leukemic T-cell infiltration into both the brain and spinal cord (see DND41/mCCR7$^{pos}$ in FIGS. 3C-3D).

Figure 4A:
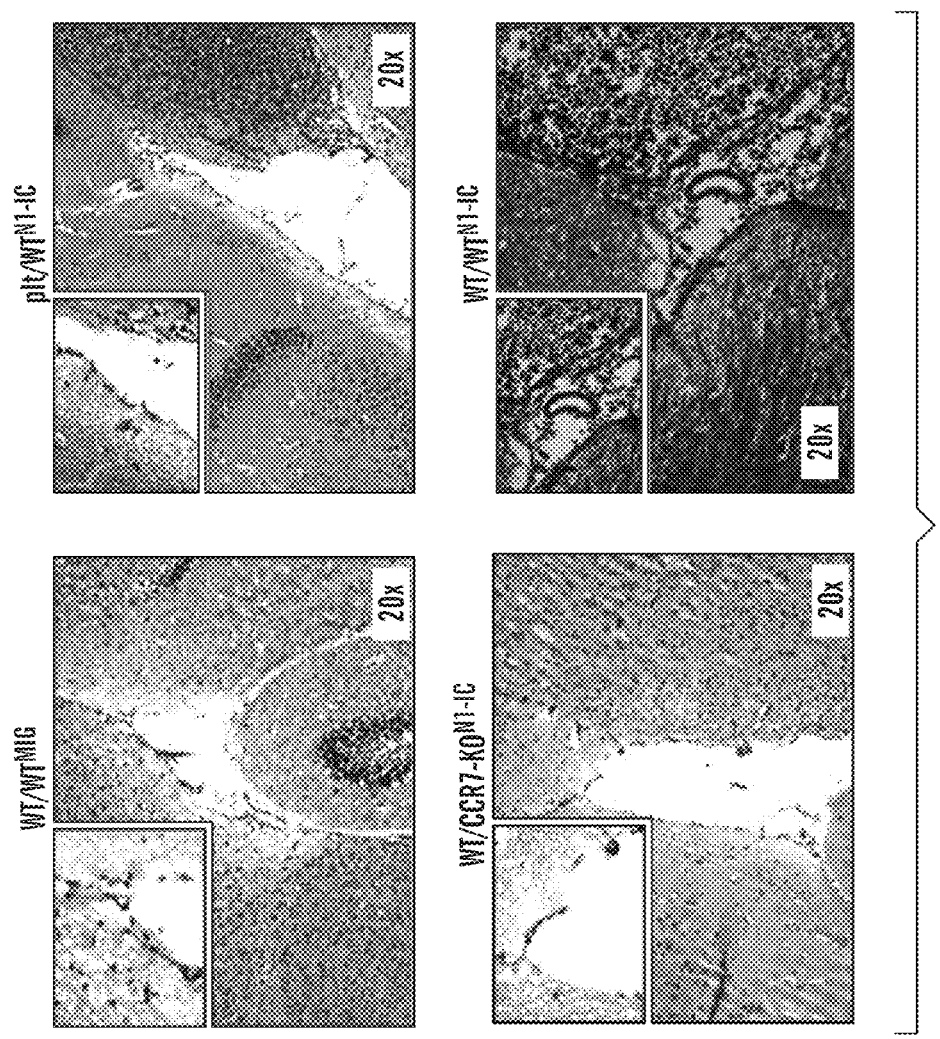
FIGS. 4A-4G demonstrate the importance of the CCR7-CCL19 interactions for CNS infiltration in animal models of T-ALL.
Figure 4B:
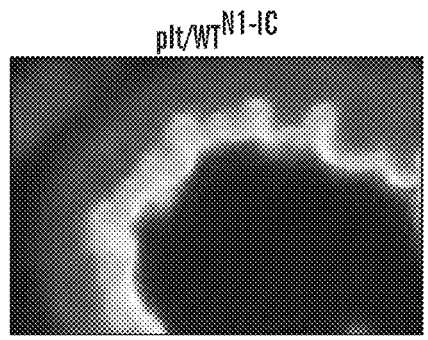
Figure 4C:
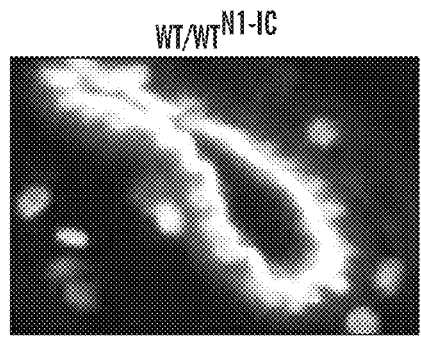
Figure 4D:
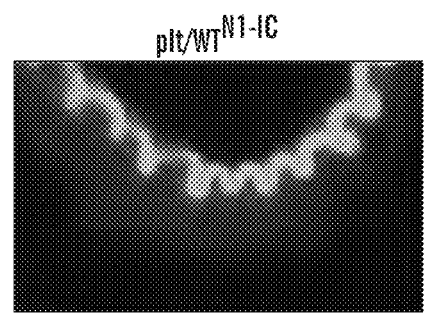
Figure 11A:
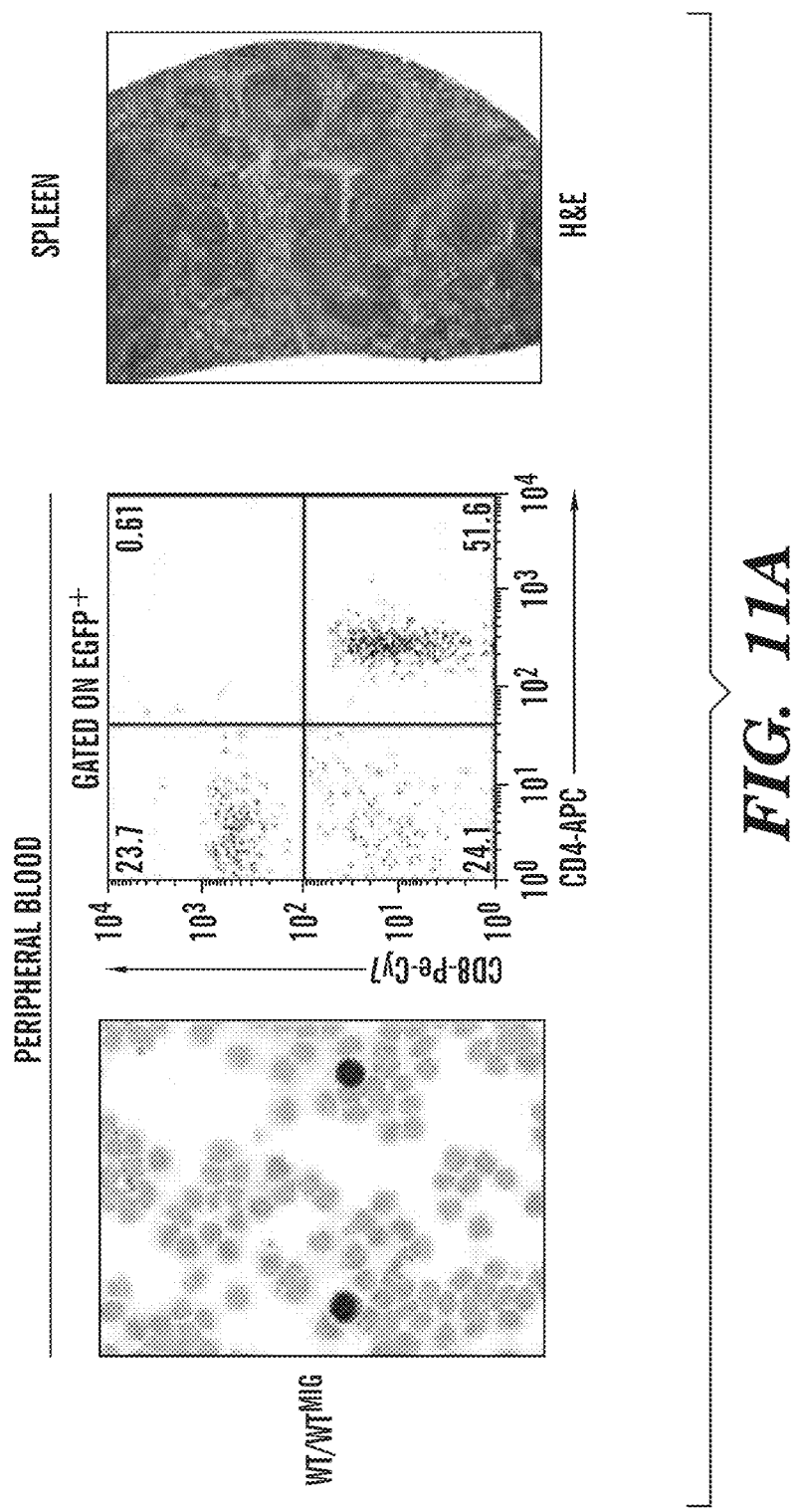
FIGS. 11A-11C depict the development of leukemia in recipient mice that either lack CCL19 expression (plt/WT$^{N1-IC}$) or have received CCR7-KO cells WT/CCR7-KO$^{N1-IC}$). Induction of T-ALL was observed in recipient mice (WT or plt) that received wildtype cells expressing Notch (WT$^{N1-IC}$) (FIG. 11C) or cells deficient in CCR7 expression (CCR7-KO$^{N1-IC}$) (FIG. 11B) as indicated by analysis of CD4$^+$/CD8$^+$ peripheral blood cells (left and middle panels) and histopathological analysis of spleen tissue (right panels). T-ALL was not induced in wildtype mice receiving hematopoietic cells containing the control vector (WT$^{MIG}$) (FIG. 11A).
Figure 11B:
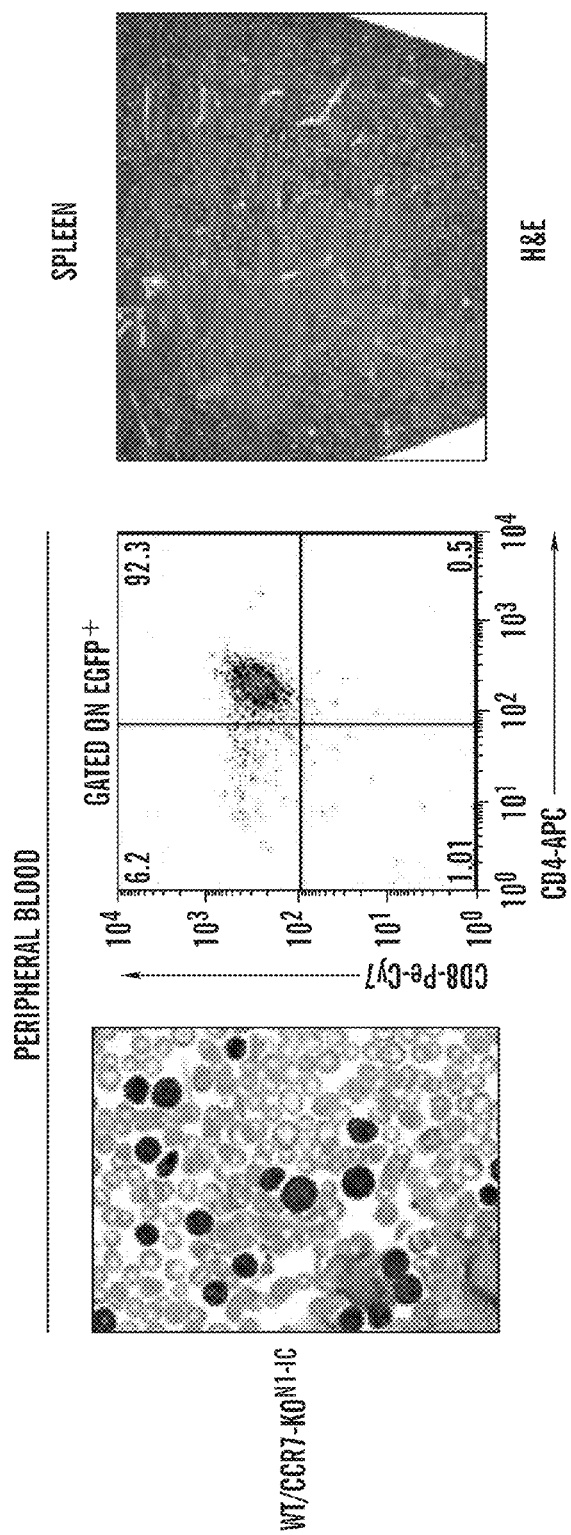
Figure 12:
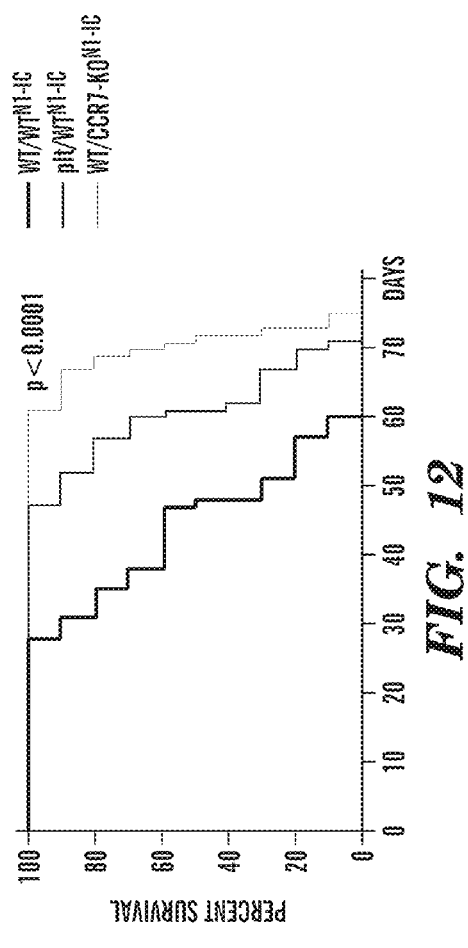
FIG. 12 shows the survival of wild-type or plt recipient mice that received leukemic cells with the indicated genotypes. Host animals receiving leukemic cells deficient in CCR7 expression (CCR7-KO$^{N1-IC}$) survived significantly longer than host animals that received leukemic wildtype cells (WT$^{N1-IC}$). p<0.0001, applies to both plt and CCR7KO groups. n=5 mice per experiment, the experiment was repeated twice.
Figure 13A:
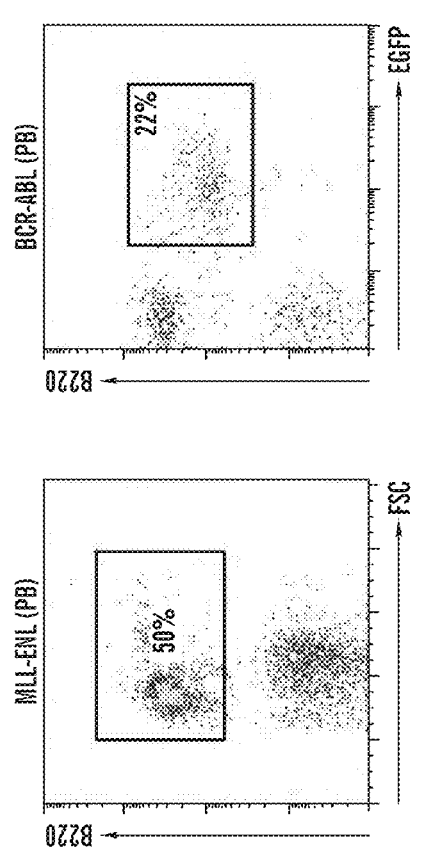
FIGS. 13A-13B demonstrate the specific requirement of CCR7 function in T-ALL CNS infiltration. B-cell acute lymphoblastic leukemia (B-ALL) was induced in recipient animals that were injected with hematopoietic progenitors infected with retroviruses carrying either the MLL-ENL/EGFP$^+$ or the BCR-ABL/EGFP$^+$ fusion genes. Leukemic B220+ cells were detected in the peripheral blood of irradiated recipients three weeks post transplant (FIG. 13A).
Figure 13B:
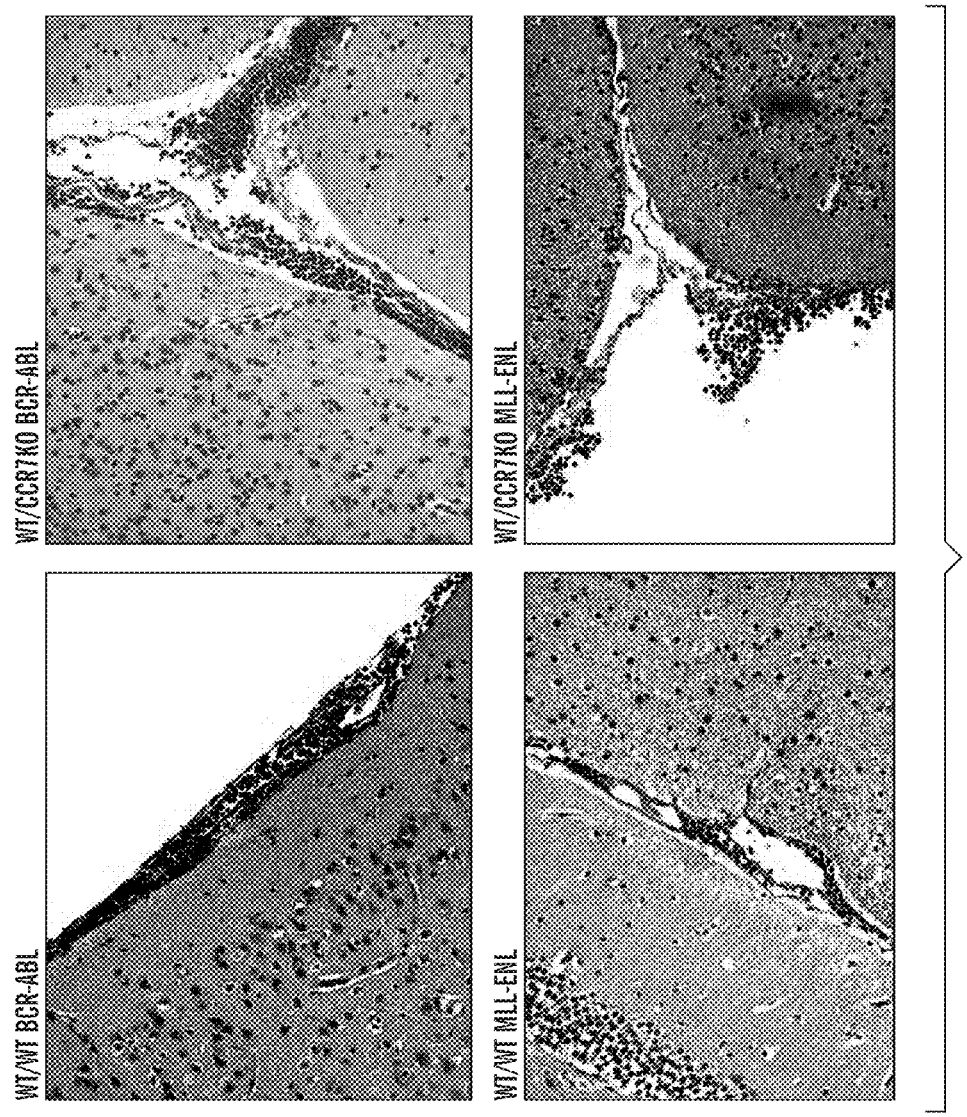
Figure 14A:
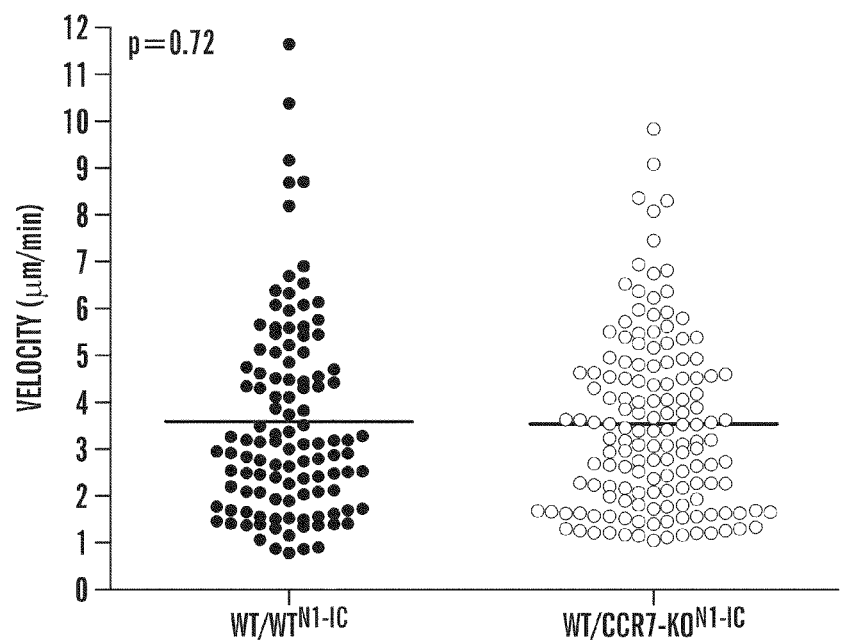
FIGS. 14A-14F show that the lack of CCR7 expression does not affect the migratory properties of leukemic T-cells. Quantitative measurements of WT$^{N1-IC}$ and CCR7-KO$^{N1-IC}$ cell velocities (FIG. 14A), turning angle (FIG. 14B), arrest coefficient (FIG. 14C), and confinement index (FIG. 14D) were made by tracking the movement of individual cells in the xy plane (parallel to the overlying capsule of the lymph node) over time. Each data point represents a single cell and black bars indicate mean values. A random walk analysis of WT$^{N1-IC}$ and CCR7-KO$^{N1-IC}$ cells was performed. The mean displacement (FIG. 14E) and mean displacement replotted as a function of the square root of time (FIG. 14F) are shown. Each data point represents the average of three different experiments. The slope of each line represents the motility coefficient M and indicates the area an average cell scans per unit time. A linear curve over time indicates a random walk, a plateau indicates confinement and a higher slope indicates directed motion (WT$^{N1-IC}$: 120 cells, 3 different mice, 3 different experiments; CCR7-KO$^{N1-IC}$: 150 cells, 4 different mice, 3 different experiments).
Figure 14B:
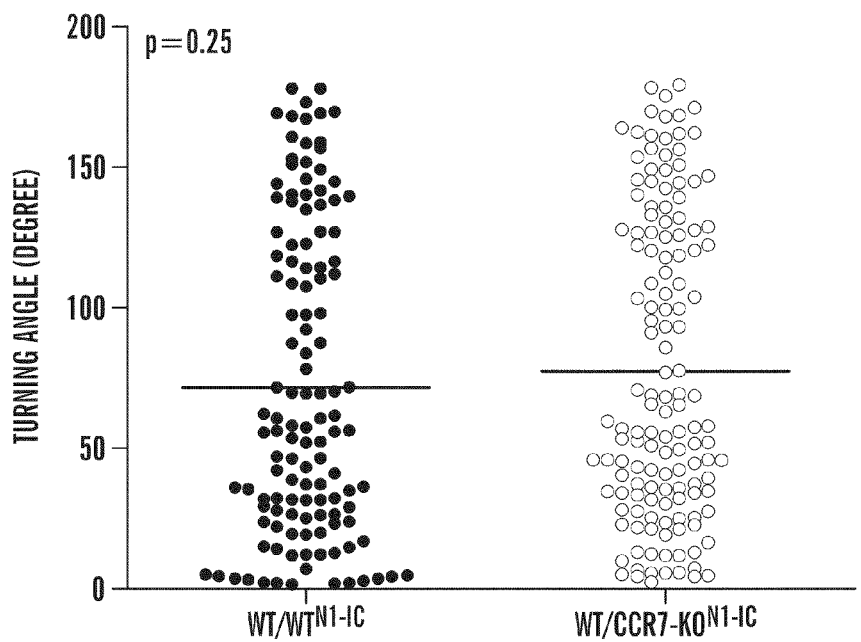
Figure 14C:
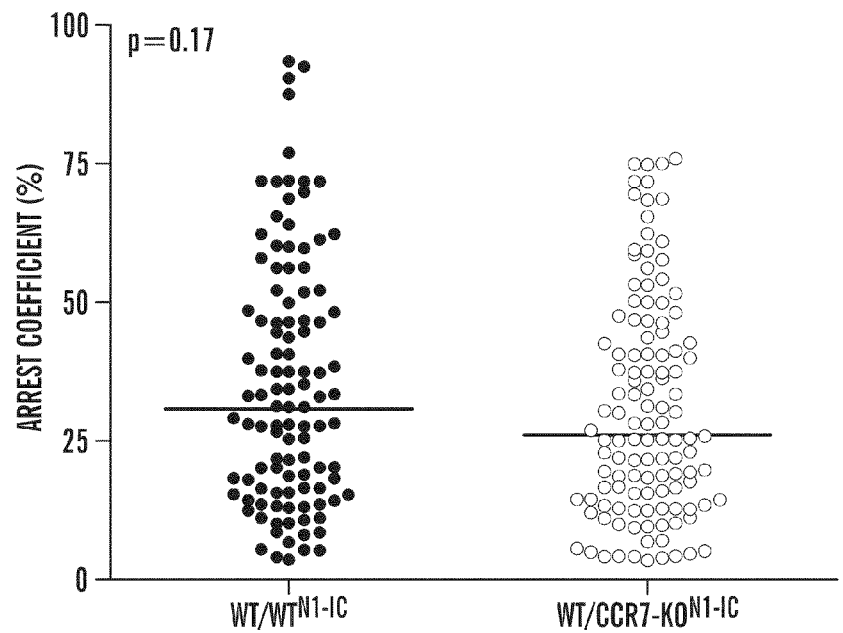
Figure 14D:
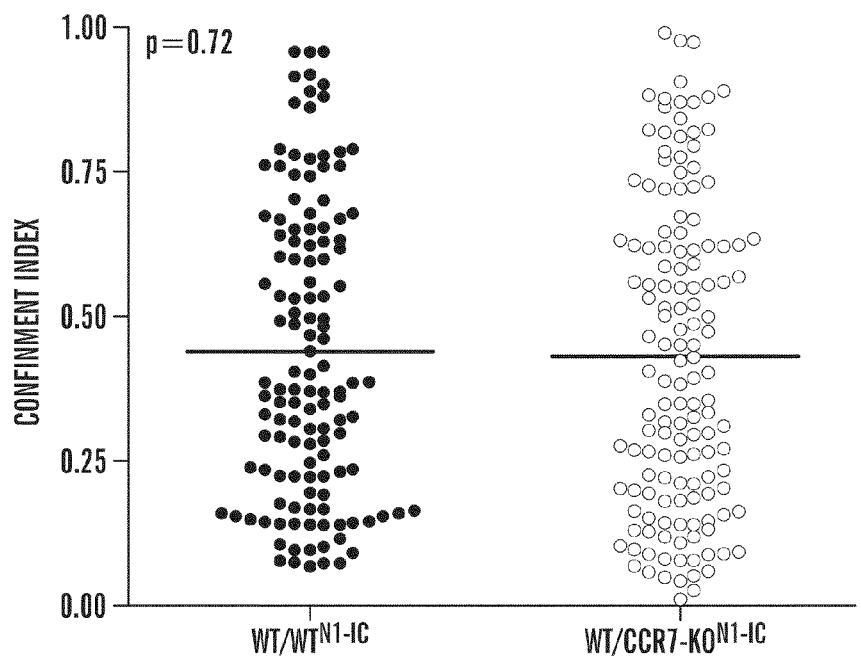
Figure 14E:
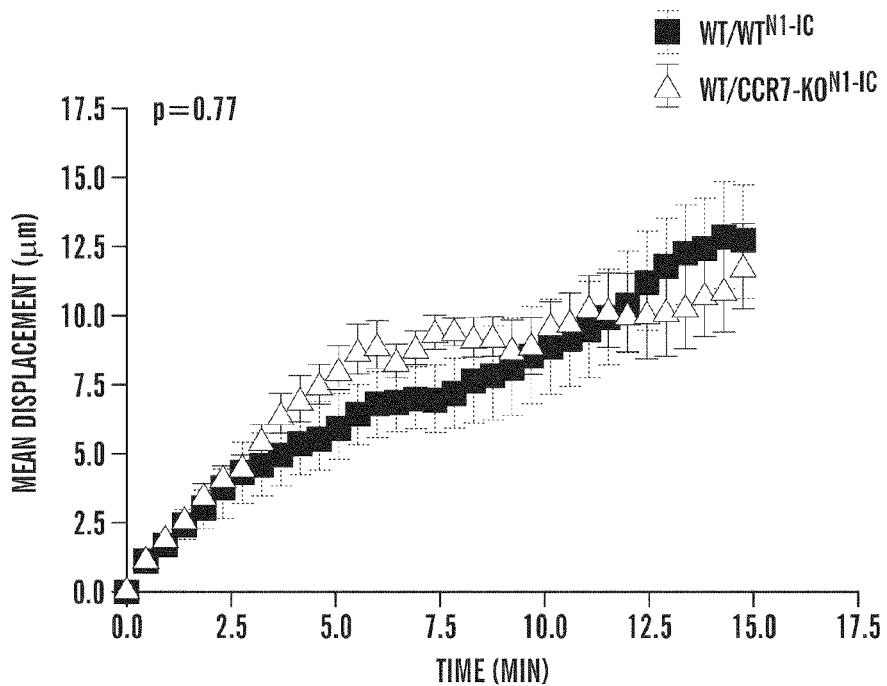
Figure 14F:
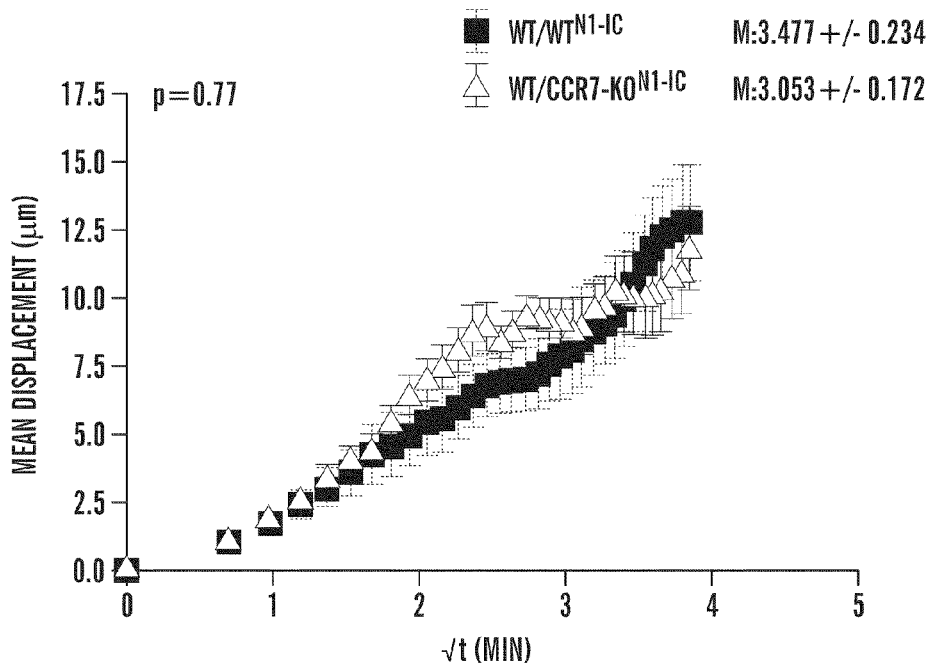

Although these results suggest that CCR7 expression is sufficient to recruit leukemic T-cells into the CNS, they do not address whether CCR7 alone is necessary for this function. Hematopoietic progenitors from CCR7-knockout (CCR7-KO) (Forster et al., "CCR7 Coordinates the Primary Immune Response by Establishing Functional Microenvironments in Secondary Lymphoid Organs," *Cell* 99:23-33 (1999), which is hereby incorporated by reference in its entirety) and CCR7-wildtype (WT) mice were infected with N1-IC and EGFP expressing retroviruses (CCR7-KO$^{N1-IC}$ and WT$^{N1-IC}$). EGFP+ cells were transplanted into WT hosts (WT/CCR7-KO$^{N1-IC}$ and WT/WT$^{N1-IC}$). All recipient mice developed T-cell leukemia, characterized by the detection of atypical peripheral blood CD4+8+ cells as soon as two weeks post-transplant (FIGS. 11A-11B). As before, histopathologic analysis showed significant tissue infiltration in all recipients (FIGS. 6A-6F). Host animals receiving leukemic CCR7-KO cells survived significantly longer than host animals that received leukemic WT cells (FIG. 12, compare WT/WT$^{N1-IC}$ and WT/CCR7-KO$^{N1-IC}$). Although both hosts had similar leukemic infiltration of most tissues, histopathological analysis of the CNS demonstrated that leukemic CCR7-KO cells did not infiltrate the brain at 5 weeks post bone marrow transplant, while leukemic WT cells did (FIG. 4A; compare WT/WT$^{N1-IC}$ and WT/CCR7-KO$^{N1-IC}$). This was also true even at later time points just before the host animals succumbed to leukemic disease, at nine to eleven weeks post transplant, uncoupling tumor load to CNS infiltration. These results suggest that CCR7 is necessary for this process, and that the elimination of a single chemokine receptor in vivo is able to abrogate CNS involvement in T-ALL. CCR7 function appears to be specific for Notch 1-induced T-cell malignancy as deletion of this chemokine in two models of B-cell acute lymphoblastic leukemia failed to suppress CNS infiltration (FIGS. 13A-13B).

To exclude the possibility that CCR7 deficient cells do not infiltrate the CNS due to a more general defect in their ability to migrate, the migration properties of CCR7-KO$^{N1-IC}$ cells was examined. As discussed supra, CCR7-KO$^{N1-IC}$ cells infiltrate as well as leukemic WT cells into several tissues. Also, the peripheral blood of hosts reconstituted with CCR7-KO$^{N1-IC}$ contained a similar (or even elevated) number of leukemic blasts (FIG. 11B). To attain a more dynamic view of the ability of the migratory properties of CCR7-KO$^{N1-IC}$ and WT$^{N1-IC}$ leukemic cells, 2-photon imaging microscopy was used to trace EGFP+ cells within the lymph nodes of living leukemic hosts. No difference in the ability of CCR7-KO$^{N1-IC}$ and WT$^{N1-IC}$ cells to migrate within the lymph nodes was observed. When individual cells were traced, no statistically significant difference between the velocity, turning angle, arrest coefficient, confinement and random walk of CCR7-KO$^{N1-IC}$ and WT$^{N1-IC}$ cells was found (FIGS. 14A-14F). These results underlined the specificity of CCR7 function in the targeting of T-ALL cells to the CNS.

Figure 4E:
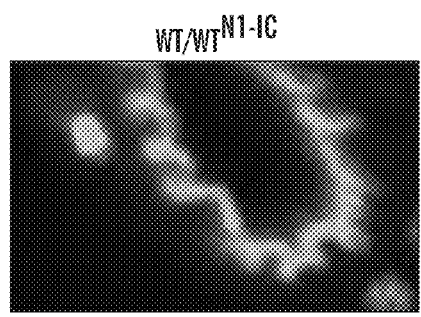
Figure 4F:
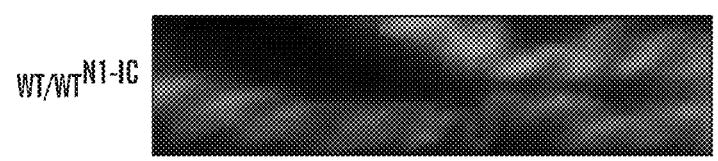
Figure 4G:
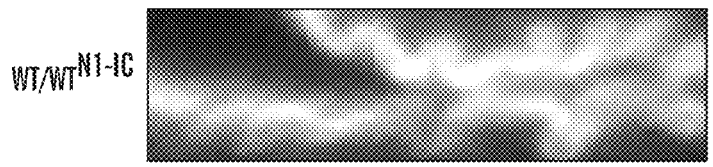
Figure 5A:
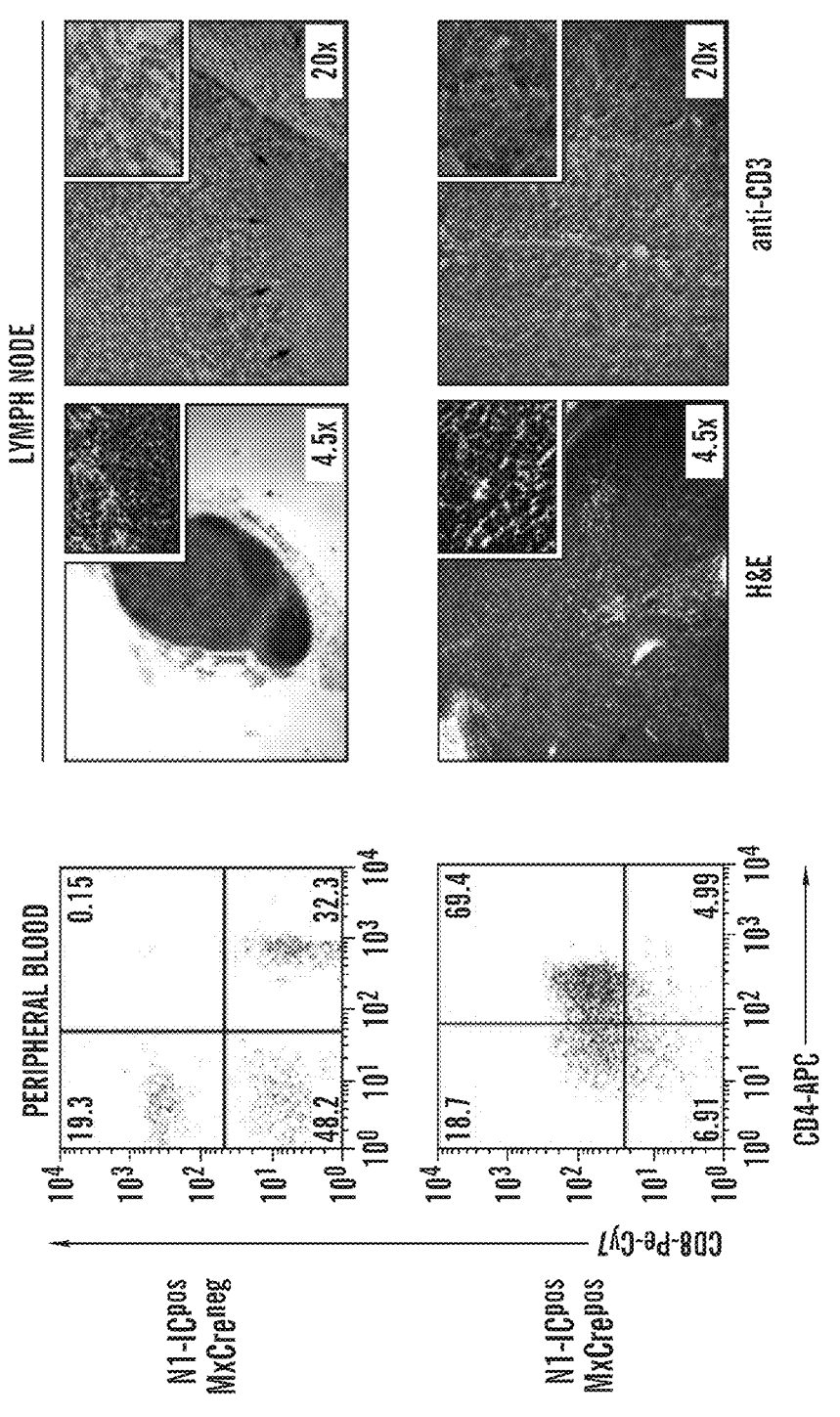
Figure 16B:
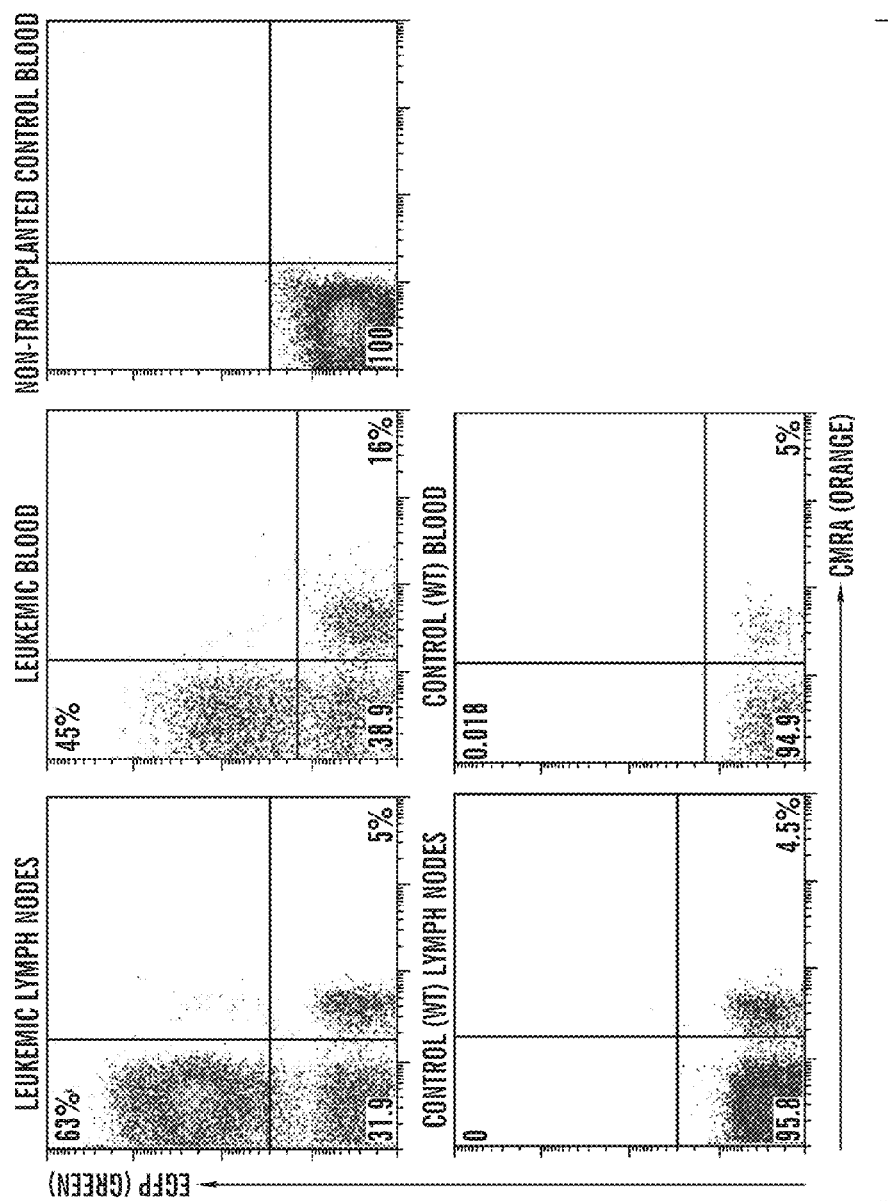
Figure 16C:
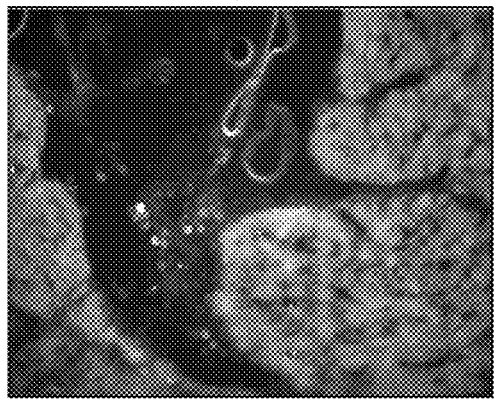

Although these studies clearly demonstrate the importance of CCR7-mediated leukemic cell recruitment to the CNS, they do not identify the ligand involved. It was previously shown that both CCR7 chemokine ligands, CCL21 and CCL19, are expressed in blood-brain barrier endothelium in an animal model of experimental autoimmune encephalomyelitis (EAE) (Kivisakk et al., "Human Cerebrospinal Fluid Central Memory CD4+ T-Cells: Evidence for Trafficking Through Choroid Plexus and Meninges via P-Selectin," *Proc Natl Acad Sci USA* 100:8389-94 (2003) and Giunti et al., "Phenotypic and Functional Analysis of T-Cells Homing into the CSF of Subjects with Inflammatory Diseases of the CNS," *J Leukoc Biol* 73:584-90 (2003), which are hereby incorporated by reference in their entirety). Moreover, CCL21 expression was detected previously in the choroid plexus, a possible site of lymphocyte entry into the subarachnoid space (Kivisakk et al., "Expression of CCR7 in Multiple Sclerosis: Implications for CNS Immunity," *Ann Neurol* 55:627-38 (2004), which is hereby incorporated by reference in its entirety). Thus, immunohistochemical analyses comparing CCL19 and CCL21 expression was performed in brain sections of control and leukemic mice. CCL21 expression was undetectable in either sample. However, CCL19 was detectable mainly in brain venules in the vicinity of infiltrating lymphocytes (FIGS. 4E and 4G). Dual immunofluorescence labeling confirmed that CD31+ endothelial cells produced CCL19 (FIGS. 4G). In addition, purified brain CD31+ endothelial cells showed a significant induction (8-10 fold when compared to CD31− brain cells) of CCL19 message (FIG. 15B). Finally, endothelial cells from leukemic animals expressed moderately higher (~2 fold) levels of CCL19 (FIG. 16A) when compared to endothelial brain cells from recipients that received EGFP-only infected cells (do not show any CNS infiltration). To prove that this slight over-expression is not by itself sufficient to attract CCR7+ T-cells in the CNS, wildtype CD4+ T-cells were transplanted into leukemic recipients. Analysis of recipient brain sections 12-16 hours post transplant failed to reveal any non-N1-IC/EGFP+ T-cell accumulation.

Figure 11C:
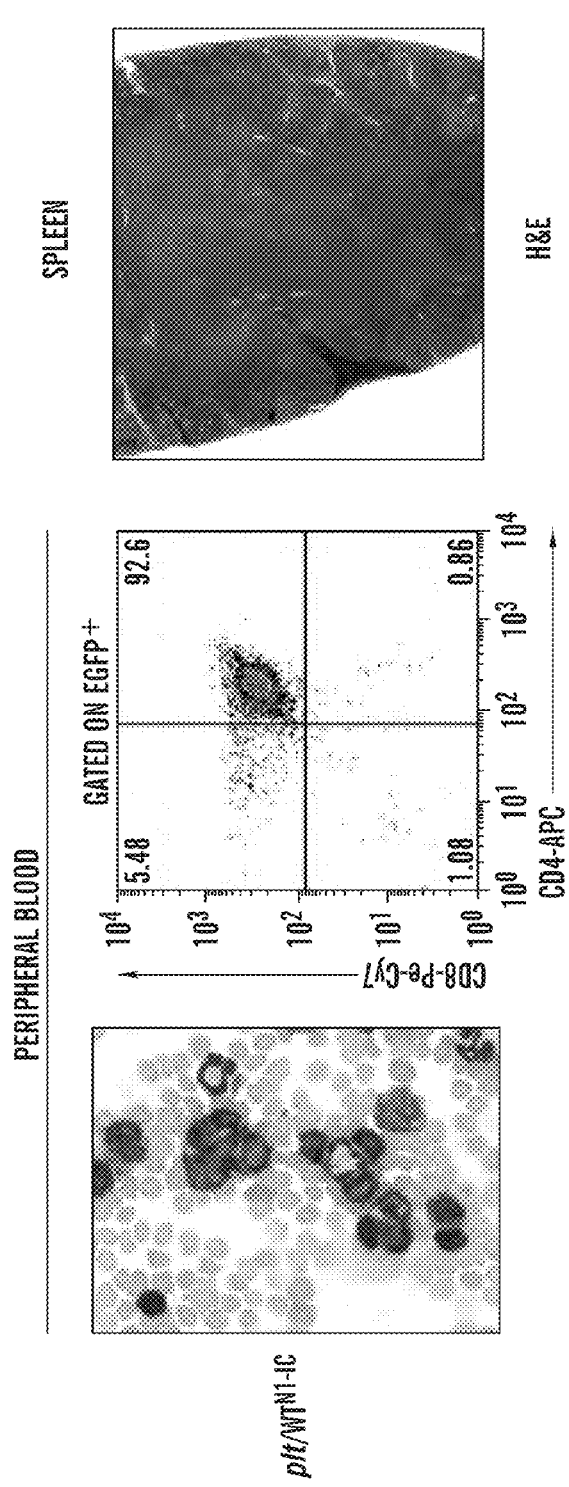

To prove the essential role of CCL19 expression, the transplantation protocol was modified to use plt mice as host animals. plt mice lack CCL19 expression due to a naturally occurring mutation (Gunn et al., "Mice Lacking Expression of Secondary Lymphoid Organ Chemokine Have Defects in Lymphocyte Homing and Dendritic Cell Localization," *J Exp Med* 189:451-60 (1999), which is hereby incorporated by reference in its entirety). These mice (or background- and age-matched controls) were transplanted with N1-IC-expressing ($WT^{N1-IC}$) hematopoietic progenitors (plt/$WT^{N1-IC}$) In agreement with previous transplantations, plt mice survived longer than their WT counterparts (FIG. 12). As before, there was an identical T-ALL induction and disease manifestation between different hosts suggesting that the plt mutation does not affect leukemic cell infiltration in peripheral lymphoid tissues (FIGS. 6G-6H and FIG. 11C). However, leukemic cells were unable to infiltrate the brain of plt host animals, further strengthening the argument that CCR7:CCL19 interactions are essential for CNS infiltration in T-ALL (compare plt/$WT^{N1-IC}$ and WT/$WT^{N1-IC}$ in FIG. 4A).

The data described herein demonstrates that a single chemokine:receptor pair is both necessary and sufficient for T-ALL leukemic cell targeting to the CNS. It should be noted that while CCR7 expression appears to be a significant signal targeting T-ALL cells in the CNS, additional factors may be involved in mediating CNS infiltration. These factors may include additional adhesion regulators (i.e., integrins, metalloprotease, see FIG. 2A) that could potentially interact with CCR7 function. These studies open the way for the development of different therapeutic protocols in which specific adhesion antagonists (Ransohoff, R. M., "Natalizumab for Multiple Sclerosis," *N Engl J Med* 356:2622-9 (2007), which is hereby incorporated by reference in its entirety) can be used in combination with either current chemotherapy based protocols or molecularly-targeted approaches, for example, the use of antagonists of Notch signaling (Grabher et al., "Notch 1 Activation in the Molecular Pathogenesis of T-Cell Acute Lymphoblastic Leukaemia," *Nat Rev Cancer* 6(5):347-59 (2006), which is hereby incorporated by reference in its entirety). Putative T-ALL CNS infiltration antagonists could include inhibitors of CCR7 expression and function as well as drugs targeting specific migration regulators that could be activated by CCR7 signaling.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of inhibiting development of central nervous system leukemia in a subject, said method comprising:
   selecting a subject having T-cell acute lymphoblastic leukemia, wherein said subject does not have central nervous system leukemia;
   providing a CCR7 antibody; and
   administering the CCR7 antibody to the selected subject under conditions effective to inhibit development of central nervous system leukemia in the selected subject.

2. The method according to claim 1, wherein the CCR7 antibody is a human monoclonal antibody or an active binding fragment thereof.

3. The method according to claim 1, further comprising:
   administering to the selected subject a therapeutic agent that inhibits Notch-1 selected from the group consisting of [(2S)-2-{[(3,5-Difluorophenyl)acetyl]amino}-N-[(3S)1-methyl-2-oxo-5-phenyl-2,3-dihydro-1 H-1, 4-benzodiazepin-3-yl] propanamide](CompE), N-[N-(3,5-difluorophenacetyl)-L-alanyl]-Sphenylglycine-t-butylester (DAPT), LY411575, (5S)-(t-Butoxycarbonylamino)-6-phenyl-(4R)hydroxy-(2R)benzylhexanoyl)-L-leu-L-phe-amide (L-685,458), L-852,647, MW167, WPE-III-31, LY450139, MRK003, R-flurbiprofen ([1, 1'-Biphenyl]-4-acetic acid, 2-fluoro-alpha- methyl), NGX-555, E2012, GSI-1, Begacestat (2-Thiophenesulfonamide, 5- chloro-N-[(1S)-3₁3,3-trifluoro-1-(hydroxymethyl)-2-(trifluoromethyl)propyl]-), NIC5-15, and CHF-5074.

4. The method according to claim 1 further comprising:
   administering a chemotherapeutic agent to the subject.

5. The method according to claim 4, wherein the chemotherapeutic agent is selected from the group consisting of cytarabine, vincristine, prednisone, daunorubicin, PEG asparaginase, methotrexate, and leucovorin.

6. A method of treating T-cell acute lymphoblastic leukemia in a subject, said method comprising:
   selecting a subject having T-cell acute lymphoblastic leukemia, wherein said subject does not have central nervous system leukemia and
   administering a cocktail of chemotherapeutic agents and a CCR7 antibody under conditions effective to treat T-cell acute lymphoblastic leukemia in the selected subject.

7. The method according to claim 6, wherein the cocktail of chemotherapeutic agents comprises two or more chemotherapeutic agents selected from the group consisting of cytarabine, vincristine, prednisone, daunorubicin, PEG asparaginase, methotrexate, and leucovorin.

8. The method according to claim 6, wherein the CCR7 antibody is a human monoclonal antibody or an active binding fragment thereof.

* * * * *